US012778538B2

(12) United States Patent
Liu et al.

(10) Patent No.: US 12,778,538 B2
(45) Date of Patent: Nov. 3, 2026

(54) SYSTEMS AND METHODS FOR FACILITATING AUTOMATED OPERATION OF A DEVICE IN A SURGICAL SPACE

(71) Applicant: Intuitive Surgical Operations, Inc., Sunnyvale, CA (US)

(72) Inventors: Wen Pei Liu, San Jose, CA (US); Mahdi Azizian, San Jose, CA (US); Azad Shademan, Campbell, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 561 days.

(21) Appl. No.: 17/911,290

(22) PCT Filed: Mar. 29, 2021

(86) PCT No.: PCT/US2021/024590
§ 371 (c)(1),
(2) Date: Sep. 13, 2022

(87) PCT Pub. No.: WO2021/202341
PCT Pub. Date: Oct. 7, 2021

(65) Prior Publication Data

US 2023/0126545 A1 Apr. 27, 2023

Related U.S. Application Data

(60) Provisional application No. 63/002,839, filed on Mar. 31, 2020.

(51) Int. Cl.
*A61B 8/08* (2006.01)
*A61B 34/20* (2016.01)

(52) U.S. Cl.
CPC ................ *A61B 8/08* (2013.01); *A61B 34/20* (2016.02)

(58) Field of Classification Search
CPC ........... A61B 8/08; A61B 34/20; A61B 90/36; A61B 34/37; A61B 34/30; A61B 90/361;
(Continued)

(56) References Cited

U.S. PATENT DOCUMENTS

| | | | | |
|---|---|---|---|---|
| 6,425,865 B1 * | 7/2002 | Salcudean | .............. | A61B 34/32 600/437 |
| 8,147,503 B2 * | 4/2012 | Zhao | ...................... | A61B 34/37 382/128 |

(Continued)

FOREIGN PATENT DOCUMENTS

| | | |
|---|---|---|
| CN | 108778179 A | 11/2018 |
| WO | WO-2016201123 A1 | 12/2016 |

(Continued)

OTHER PUBLICATIONS

International Search Report and Written Opinion for Application No. PCT/US2021/024590, mailed Jul. 7, 2021, 15 pages.

(Continued)

*Primary Examiner* — Stephen S Hong
*Assistant Examiner* — Carl E Barnes, Jr.

(57) ABSTRACT

An exemplary system includes a memory storing instructions and a processor communicatively coupled to the memory. The processor may be configured to execute the instructions to obtain one or more operating characteristics of an instrument located in a surgical space; obtain one or more anatomical characteristics associated with the surgical space; and direct a computer-assisted surgical system to automatically perform, based on the based on the one or more operating characteristics of the device and the one or more anatomical characteristics associated with the surgical space, an operation with the instrument located in the surgical space.

18 Claims, 11 Drawing Sheets

(58) Field of Classification Search
CPC .............. A61B 90/37; A61B 2034/101; A61B 2090/3612; A61B 2017/00477; A61B 2017/00221; A61B 2017/00203; A61B 2017/00207; A61B 2034/107; A61B 2017/00225; A61B 2090/365; A61B 2017/00216; A61B 2090/3782; A61B 2090/067; A61B 2090/367; A61B 2034/2065; A61B 2017/00128
See application file for complete search history.

(56) References Cited

U.S. PATENT DOCUMENTS

| | | | | |
|---|---|---|---|---|
| 9,826,904 | B2 * | 11/2017 | Valdastri | A61B 5/0031 |
| 11,058,505 | B2 * | 7/2021 | Venkataraman | A61B 34/74 |
| 2004/0106916 | A1 * | 6/2004 | Quaid | A61B 34/71<br>606/1 |
| 2006/0241414 | A1 * | 10/2006 | Nowlin | A61B 34/35<br>600/431 |
| 2008/0130965 | A1 * | 6/2008 | Avinash | A61B 90/36<br>382/128 |
| 2017/0143429 | A1 * | 5/2017 | Richmond | A61B 34/37 |
| 2017/0172674 | A1 * | 6/2017 | Hanuschik | A61B 34/30 |
| 2017/0189127 | A1 * | 7/2017 | Weir | A61B 34/20 |
| 2018/0042680 | A1 * | 2/2018 | DiMaio | G16H 20/40 |
| 2018/0153632 | A1 | 6/2018 | Tokarchuk et al. | |
| 2019/0015163 | A1 * | 1/2019 | Abhari | H04N 7/181 |
| 2019/0060013 | A1 * | 2/2019 | McDowall | G02B 23/2415 |
| 2019/0133689 | A1 * | 5/2019 | Johnson | G09B 9/00 |
| 2020/0015901 | A1 | 1/2020 | Scheib et al. | |
| 2020/0188046 | A1 * | 6/2020 | Overmyer | A61B 34/20 |
| 2021/0196109 | A1 * | 7/2021 | Shelton, IV | A61B 90/30 |
| 2021/0290317 | A1 * | 9/2021 | Sen | A61B 34/70 |

FOREIGN PATENT DOCUMENTS

| | | | | |
|---|---|---|---|---|
| WO | WO-2017098505 | A1 * | 6/2017 | A61B 34/20 |
| WO | WO-2018152183 | A1 * | 8/2018 | A61B 34/25 |
| WO | WO-2018226756 | A1 | 12/2018 | |
| WO | WO-2019132781 | A1 | 7/2019 | |

OTHER PUBLICATIONS

International Preliminary Report on Patentability for Application No. PCT/US2021/024590, mailed Oct. 13, 2022, 10 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SYSTEMS AND METHODS FOR FACILITATING AUTOMATED OPERATION OF A DEVICE IN A SURGICAL SPACE

RELATED APPLICATIONS

The present application claims priority to U.S. Provisional Patent Application No. 63/002,839, filed Mar. 31, 2020, the contents of which are hereby incorporated by reference in their entirety.

BACKGROUND INFORMATION

A computer-assisted surgical system that employs robotic and/or teleoperation technology typically includes a stereoscopic image viewer configured to provide, for display to a surgeon, imagery of a surgical space as captured by an imaging device such as an endoscope. While the surgeon's eyes are positioned in front of viewing lenses of the stereoscopic image viewer, the surgeon may view the imagery of the surgical space while remotely manipulating one or more surgical instruments located within the surgical space. The surgical instruments are attached to one or more manipulator arms of a surgical instrument manipulating system included as part of the computer-assisted surgical system.

In addition to the surgical instruments that are attached to the one or more manipulator arms, additional instruments may be inserted into the surgical space to facilitate the surgeon performing procedures within the surgical space. For example, subsurface sensing devices (e.g., ultrasound devices) may be provided within the surgical space to improve the surgeon's perception of the surgical space and improve an outcome of a procedure. However, such additional instruments are not typically integrated into a module that attaches to a manipulator arm of a computer-assisted surgical system. In view of this, such additional instruments may only be available as drop-in instruments that rely on, for example, a grasper surgical instrument attached to a manipulator arm of a computer-assisted surgical system to grasp and move the drop-in instruments within the surgical space. Operation of a teleoperated grasper surgical instrument to interact with a drop-in instrument requires a surgeon to perform complex maneuvers to pick up and use the drop-in instrument within the surgical space. In addition, use of an instrument such as a drop-in ultrasound probe may be cumbersome and/or time consuming in instances where a surgeon has to repeatedly switch between teleoperating surgical instruments located in the surgical space and teleoperating the drop-in instrument to capture imagery of the surgical space.

SUMMARY

An exemplary system comprises a memory storing instructions; and a processor communicatively coupled to the memory and configured to execute the instructions to: obtain one or more operating characteristics of an device located in a surgical space; obtain one or more anatomical characteristics associated with the surgical space; and direct a computer-assisted surgical system to automatically perform, based on the one or more operating characteristics of the device and the one or more anatomical characteristics associated with the surgical space, an operation with the device located in the surgical space.

An additional exemplary system comprises a memory storing instructions; and a processor communicatively coupled to the memory and configured to execute the instructions to: obtain one or more operating characteristics of a non-robotic device that is engaged by a first robotic instrument in a surgical space, wherein the first robotic instrument, a second robotic instrument, and a third robotic instrument are each attached to a computer-assisted surgical system, and the second and third robotic instruments are configured to be bimanually teleoperated by a user of the computer-assisted surgical system; obtain one or more anatomical characteristics associated with the surgical space; and direct the computer-assisted surgical system to automatically perform, based on the one or more operating characteristics of the device and the one or more anatomical characteristics associated with the surgical space, an operation with the non-robotic device while the user of the computer-assisted surgical system bimanually teleoperates the second and third robotic instruments.

An exemplary method comprises obtaining, by a processor associated with a computer-assisted surgical system, one or more operating characteristics of a device located in a surgical space; obtaining, by the processor, one or more anatomical characteristics associated with the surgical space; and directing, by the processor, the computer-assisted surgical system to automatically perform, based on the one or more operating characteristics of the device and the one or more anatomical characteristics associated with the surgical space, an operation with the device located in the surgical space.

An exemplary non-transitory tangible computer program product comprises a tangible computer readable medium configured to store computer readable instructions that are executable by a processor to: obtain one or more operating characteristics of an device located in a surgical space; obtain one or more anatomical characteristics associated with the surgical space; and direct a computer-assisted surgical system to automatically perform, based on the one or more operating characteristics of the device and the one or more anatomical characteristics associated with the surgical space, an operation with the device located in the surgical space.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
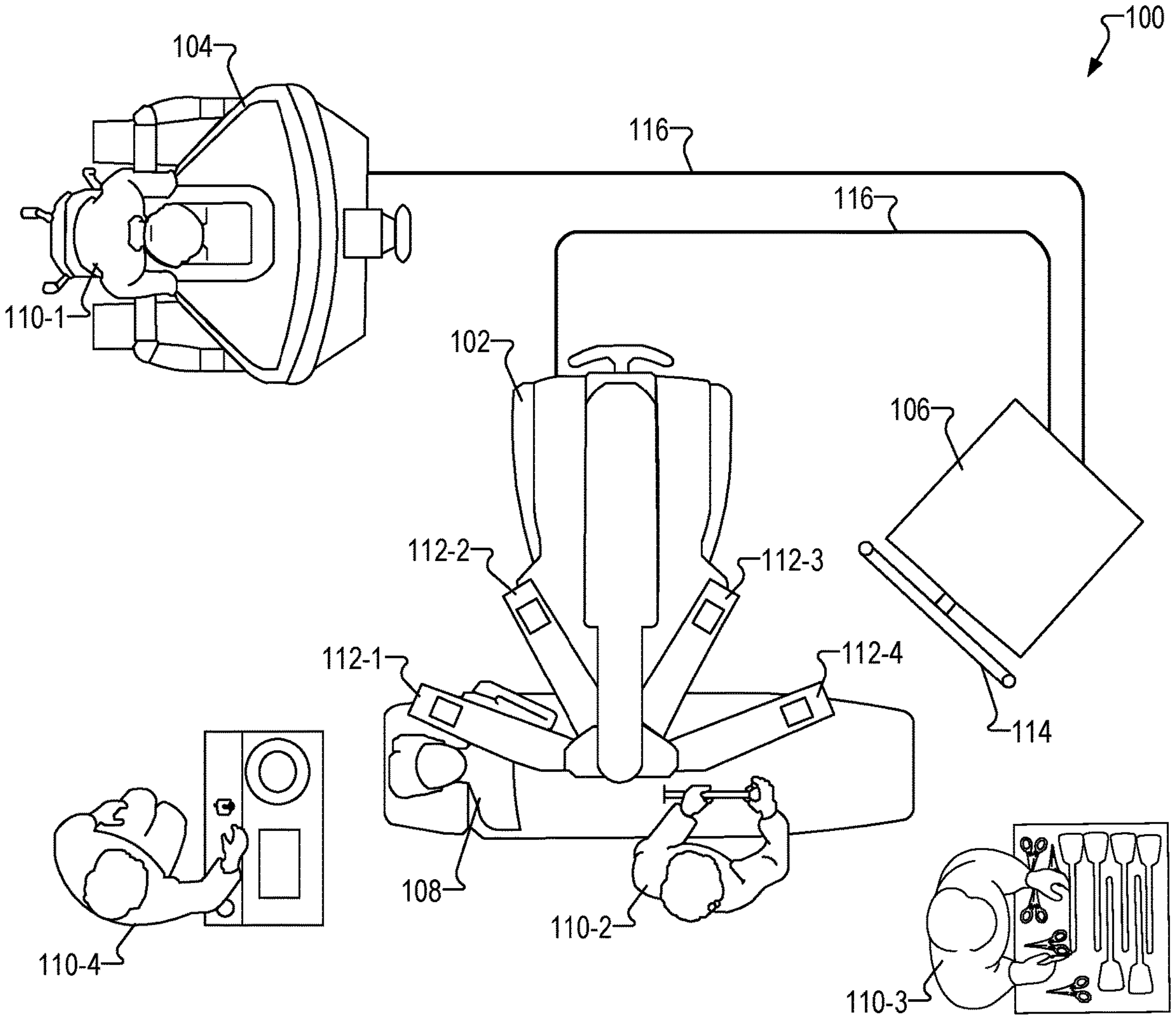
FIG. 1 illustrates an exemplary computer-assisted surgical system according to principles described herein.

Systems and methods for facilitating automated operation of a device in a surgical space are described herein. As will be described in more detail below, an exemplary system includes a memory that stores instructions and a processor communicatively connected to the memory. The processor of the exemplary system is configured to obtain one or more operating characteristics of a device located in a surgical space; obtain one or more anatomical characteristics associated with the surgical space; and direct a computer-assisted surgical system to automatically perform, based on the one or more operating characteristics of the device and the one or more anatomical characteristics associated with the surgical space, an operation with the device located in the surgical space.

Various advantages and benefits are associated with systems and methods described herein. For example, systems and methods such as those described herein may reduce the mental and/or physical workload required for a user of a computer-assisted surgical system (e.g., a surgeon and/or another user associated with a computer-assisted surgical system) to use (e.g., teleoperate) one or more robotic instruments located in a surgical space, such as by the systems and methods facilitating a device automatically moving and/or operating in the surgical space. In so doing, systems and methods such as those described herein may simplify procedures performed within the surgical space and/or improve usability of a computer-assisted surgical system. These and other benefits that may be realized by the systems and methods described herein will be evident from the disclosure that follows.

Exemplary systems described herein may be configured to operate as part of or in conjunction with a plurality of different types of computer-assisted surgical systems. The plurality of different types of computer-assisted surgical systems may be of different types at least because they include different types of surgical instrument manipulating systems. For example, a first computer-assisted surgical system may include a first type of surgical instrument manipulating system, a second computer-assisted surgical system may include a second type of surgical instrument manipulating system, and a third computer-assisted surgical system may include a third type of surgical instrument manipulating system.

Each type of surgical instrument manipulating system may have a different architecture (e.g., a manipulator arm architecture), have a different kinematic profile, and/or operate according to different configuration parameters. An exemplary computer-assisted surgical system with a first type of surgical instrument manipulating system will now be described with reference to FIG. 1. The described exemplary computer-assisted surgical system is illustrative and not limiting. Systems such as those described herein may operate as part of or in conjunction with the described computer-assisted surgical system and/or any other suitable computer-assisted surgical system.

FIG. 1 illustrates an exemplary computer-assisted surgical system 100 ("surgical system 100"). As shown, surgical system 100 may include a surgical instrument manipulating system 102 ("manipulating system 102"), a user control system 104, and an auxiliary system 106 communicatively coupled one to another.

Surgical system 100 may be utilized by a surgical team to perform a computer-assisted surgical procedure on a patient 108. As shown, the surgical team may include a surgeon 110-1, an assistant 110-2, a nurse 110-3, and an anesthesiologist 110-4, all of whom may be collectively referred to as "surgical team members 110." Additional or alternative surgical team members may be present during a surgical session as may serve a particular implementation.

While FIG. 1 illustrates an ongoing minimally invasive surgical procedure, surgical system 100 may similarly be used to perform open surgical procedures or other types of surgical procedures that may similarly benefit from the accuracy and convenience of surgical system 100. Additionally, it will be understood that the surgical session throughout which surgical system 100 may be employed may not only include an operative phase of a surgical procedure, as is illustrated in FIG. 1, but may also include preoperative, postoperative, and/or other suitable phases of the surgical procedure. A surgical procedure may include any procedure in which manual and/or instrumental techniques (e.g., teleoperated instrumental techniques) are used on a patient to investigate, diagnose, or treat a physical condition of the patient. Additionally, a surgical procedure may include any procedure that is not performed on a live patient, such as a calibration procedure, a simulated training procedure, and an experimental or research procedure.

As shown in FIG. 1, surgical instrument manipulating system 102 may include a plurality of manipulator arms 112 (e.g., manipulator arms 112-1 through 112-4) to which a plurality of robotic surgical instruments ("robotic instruments") (not shown) may be coupled. As used herein, a "robotic instrument" refers to any instrument that may be directly attached to (e.g., plugged into, fixedly coupled to, mated to, etc.) a manipulator arm (e.g., manipulator arm 112-1) such that movement of the manipulator arm directly causes movement of the instrument. Each robotic instrument may be implemented by any suitable therapeutic instrument (e.g., a tool having tissue-interaction functions), imaging device (e.g., an endoscope), diagnostic instrument, or the like that may be used for a computer-assisted surgical procedure (e.g., by being at least partially inserted into patient 108 and manipulated to perform a computer-assisted surgical procedure on patient 108). In some examples, one or more of the robotic instruments may include force-sensing and/or other sensing capabilities.

In the example shown in FIG. 1, manipulator arms 112 of manipulating system 102 are attached on a distal end of an overhead boom that extends horizontally. However, manipulator arms 112 may have other configurations in certain implementations. In addition, while manipulating system 102 is depicted and described herein as including four manipulator arms 112, it will be recognized that manipulating system 102 may include only a single manipulator arm 112 or any other number of manipulator arms as may serve a particular implementation.

Manipulator arms 112 and/or robotic instruments attached to manipulator arms 112 may include one or more displacement transducers, orientational sensors, and/or positional sensors (hereinafter "surgical system sensors") used to generate raw (e.g., uncorrected) kinematics information. One or more components of surgical system 100 may be configured to use the kinematics information to track (e.g., determine positions of) and/or control the robotic instruments.

In addition, manipulator arms 112 may each include or otherwise be associated with a plurality of motors that control movement of manipulator arms 112 and/or the surgical instruments attached thereto. For example, manipulator arm 112-1 may include or otherwise be associated with a first internal motor (not explicitly shown) configured to yaw manipulator arm 112-1 about a yaw axis. In like manner, manipulator arm 112-1 may be associated with a second internal motor (not explicitly shown) configured to drive and pitch manipulator arm 112-1 about a pitch axis. Likewise, manipulator arm 112-1 may be associated with a third internal motor (not explicitly shown) configured to slide manipulator arm 112-1 along insertion axis. Manipulator arms 112 may each include a drive train system driven by one or more of these motors in order to control the pivoting of manipulator arms 112 in any manner as may serve a particular implementation. As such, if a robotic instrument attached, for example, to manipulator arm 112-1 is to be mechanically moved, one or more of the motors coupled to the drive train may be energized to move manipulator arm 112-1.

Robotic instruments attached to manipulator arms 112 may each be positioned in a surgical space. A "surgical space" may, in certain examples, be entirely disposed within a patient and may include an area within the patient at or near where a surgical procedure is planned to be performed, is being performed, or has been performed. For example, for a minimally invasive surgical procedure being performed on tissue internal to a patient, the surgical space may include the tissue, anatomy underlying the tissue, as well as space around the tissue where, for example, robotic instruments and/or other instruments being used to perform the surgical procedure are located. In other examples, a surgical space may be at least partially disposed external to the patient at or near where a surgical procedure is planned to be performed, is being performed, or has been performed on the patient. For instance, surgical system 100 may be used to perform an open surgical procedure such that part of the surgical space (e.g., tissue being operated on) is internal to the patient while another part of the surgical space (e.g., a space around the tissue where one or more instruments may be disposed) is external to the patient. A robotic instrument may be referred to as being positioned or located at or within a surgical space when at least a portion of the robotic instrument (e.g., a distal portion of the robotic instrument) is located within the surgical space. Exemplary surgical spaces and/or images of surgical spaces will be described herein.

User control system 104 may be configured to facilitate control by surgeon 110-1 of manipulator arms 112 and robotic instruments attached to manipulator arms 112. For example, surgeon 110-1 may interact with user control system 104 to remotely move, manipulate, or otherwise teleoperate manipulator arms 112 and the robotic instruments. To this end, user control system 104 may provide surgeon 110-1 with imagery (e.g., high-definition three-dimensional (3D) imagery) of a surgical space associated with patient 108 as captured by an imaging device. In certain examples, user control system 104 may include a stereoscopic image viewer having two displays where stereoscopic images (e.g., 3D images) of a surgical space associated with patient 108 and generated by a stereoscopic imaging system may be viewed by surgeon 110-1. Surgeon 110-1 may utilize the imagery to perform one or more procedures with one or more robotic instruments attached to manipulator arms 112.

To facilitate control of robotic instruments, user control system 104 may include a set of master controls (not shown). These master controls may be manipulated by surgeon 110-1 to control movement of robotic instruments (e.g., by utilizing robotic and/or teleoperation technology). The master controls may be configured to detect a wide variety of hand, wrist, and finger movements by surgeon 110-1. In this manner, surgeon 110-1 may intuitively perform a surgical procedure using one or more robotic instruments.

User control system 104 may further be configured to facilitate control by surgeon 110-1 of other components of surgical system 100. For example, surgeon 110-1 may interact with user control system 104 to change a configuration or operating mode of surgical system 100, to change a display mode of surgical system 100, to generate additional control signals used to control surgical instruments attached to manipulator arms 112, to facilitate switching control from one robotic instrument to another, to facilitate interaction with other instruments and/or objects within the surgical space, or to perform any other suitable operation. To this end, user control system 104 may also include one or more input devices (e.g., foot pedals, buttons, switches, etc.) configured to receive input from surgeon 110-1.

Auxiliary system 106 may include one or more computing devices configured to perform primary processing operations of surgical system 100. The one or more computing devices included in auxiliary system 106 may control and/or coordinate operations performed by various other components (e.g., manipulating system 102 and/or user control system 104) of surgical system 100. For example, a computing device included in user control system 104 may transmit instructions to manipulating system 102 by way of the one or more computing devices included in auxiliary system 106. As another example, auxiliary system 106 may receive, from manipulating system 102, and process image data representative of imagery captured by an imaging device attached to one of manipulator arms 112.

In some examples, auxiliary system 106 may be configured to present visual content to surgical team members 110 who may not have access to the images provided to surgeon 110-1 at user control system 104. To this end, auxiliary system 106 may include a display monitor 114 configured to display one or more user interfaces, such as images (e.g., 2D images) of the surgical space, information associated with patient 108 and/or the surgical procedure, and/or any other visual content as may serve a particular implementation. For example, display monitor 114 may display images of the surgical space together with additional content (e.g., representations of target objects, graphical content, contextual information, etc.) concurrently displayed with the images. In some embodiments, display monitor 114 is implemented by a touchscreen display with which surgical team members 110 may interact (e.g., by way of touch gestures) to provide user input to surgical system 100.

Manipulating system 102, user control system 104, and auxiliary system 106 may be communicatively coupled one to another in any suitable manner. For example, as shown in FIG. 1, manipulating system 102, user control system 104, and auxiliary system 106 may be communicatively coupled by way of control lines 116, which may represent any wired or wireless communication link as may serve a particular implementation. To this end, manipulating system 102, user control system 104, and auxiliary system 106 may each include one or more wired or wireless communication interfaces, such as one or more local area network interfaces, Wi-Fi network interfaces, cellular interfaces, etc.

Figure 2:
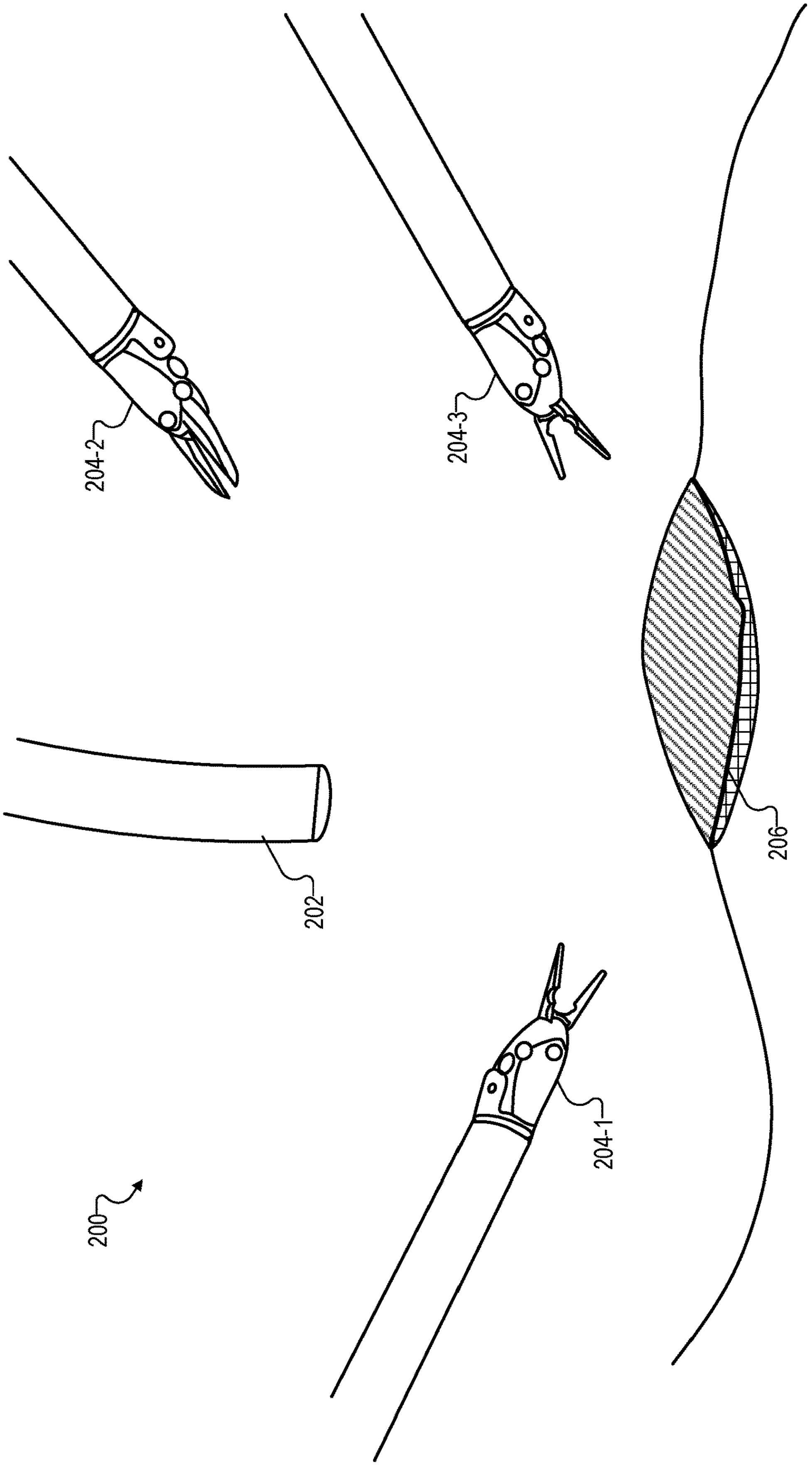
FIG. 2 illustrates an exemplary view of a surgical space according to principles described herein.

FIG. 2 illustrates a view 200 of a surgical space in which various robotic instruments are attached to manipulator arms 112 of surgical system 100. As shown, the robotic instruments may include an imaging device 202 and one or more other robotic instruments 204 (e.g., robotic instruments 204-1 through 204-3) in the form of one or more surgical tools. While FIG. 2 shows one imaging device 202 and three other robotic instruments 204 located at the surgical space, any number, type, and/or combination of robotic instruments may be at the surgical space during a surgical procedure. In the example shown in FIG. 2, robotic instruments 204-1 and 204-3 are shown as grasping-type robotic instruments whereas robotic instrument 204-2 is shown as a cutting-type robotic instrument. It is understood that other types of robotic instruments (e.g., diagnostic tools, therapeutic tools, etc.) different than those shown in FIG. 2 may additionally or alternatively be provided within the surgical space during the surgical procedure in certain implementations. Tissue 206 represents anatomical tissue at the surgical space.

Imaging device 202 may capture imagery at the surgical space. Any of robotic instruments 204 and/or tissue 206 that are within a field of view of imaging device 202 may be depicted in the imagery captured by imaging device 202.

Imaging device 202 may provide data representing visible light data of a surgical space. For example, imaging device 202 may capture visible light images of the surgical space that represent visible light sensed by imaging device 202. Visible light images may include images that use any suitable color and/or grayscale palette to represent a visible light-based view of the surgical space.

Imaging device 202 may also provide data representing depth data of a surgical space or data that may be processed to derive depth data of the surgical space. For example, imaging device 202 may capture images of the surgical space that represent depth sensed by imaging device 202. Alternatively, imaging device 202 may capture images of the surgical space that may be processed to derive depth data of the surgical space. The depth information may be represented as depth images (e.g., depth map images obtained using a Z-buffer that indicates distance from imaging device 202 to each pixel point on an image of a surgical space), which may be configured to visually indicate depths of objects in the surgical space in any suitable way, such as by using different greyscale values to represent different depth values. Images captured by an imaging device (e.g., by imaging device 202) and/or derived from images captured by the imaging device (e.g., visible light images and depth images) may be used to facilitate detecting a robotic instrument (e.g., robotic instruments 204-1 through 204-3) and/or one or more objects within a surgical space, such as described herein.

During a surgical procedure, it may be desirable to have a computer-assisted surgical system automatically operate a device located in a surgical space. As used herein, the expression "automatically" means that an operation (e.g., moving a device) or series of operations are performed without requiring further input from a user. For example, a computer-assisted surgical system may automatically control movement and/or operation of a device (e.g., surgical instrument 204-1 or imaging device 202) in a surgical space while a user (e.g., surgeon 110-1) bimanually teleoperates robotic instruments (e.g., robotic instruments 204-2 and 204-3) in the surgical space (e.g., by manipulating master controls of user control system 104). Exemplary operations that a computer-assisted surgical system may automatically perform with a device in a surgical space are described herein.

As used herein, a "device" may correspond to any suitable device (e.g., an instrument) that may be located in a surgical space and that may be automatically operated by a computer-assisted surgical system. In certain examples, a device may correspond to a robotic instrument that is directly attached (e.g., plugged into) one of manipulator arms 212. For example, one or more of robotic instruments 204 shown in FIG. 2 may correspond to a device that is automatically operated by a computer-assisted surgical system in certain implementations. Alternatively, a device may correspond to a non-robotic device located within a surgical space. As used herein, a "non-robotic device" refers to any suitable device or instrument that may be provided within a surgical space but that is not directly attached to one of manipulator arms 112, As such, a non-robotic device may only be movable within a surgical space by being manually manipulated by a user (e.g., surgeon 110-1, assistant 110-2, etc.), by being teleoperated by a user by way of a robotic instrument directly attached to one of manipulator arms 212 (e.g., by being grasped or otherwise engaged by robotic instrument 204-3), or by being automatically operated by a computer-assisted surgical system automatically moving a robotic instrument when the non-robotic instrument is engaged by the robotic device. As such, a non-robotic device may be referred to as a drop-in surgical instrument/device. Examples of non-robotic devices may include, but are not limited to, a non-robotic imaging device (e.g., a drop-in ultrasound probe, a drop-in optical coherence tomography ("OCT") probe, a drop-in rapid evaporative ionization mass spectrometry ("REIMS") device), a suction device, an irrigation device, a retractor device, a suture needle, and/or any other suitable device.

Non-robotic devices such as those described herein may be configured to be engaged by a robotic instrument (e.g., robotic instrument 204-1 or 204-3) in any suitable manner. For example, in certain implementations, a non-robotic device may be configured to be grasped by a grasper robotic instrument. To that end, in certain examples, a non-robotic device may include one or more graspable portions (e.g., protrusions, loops, etc.) that a robotic instrument may grasp to facilitate user teleoperation of the non-robotic device. In certain alternative implementations, a non-robotic device may be engaged by a robotic instrument without specifically being grasped by the robotic instrument. For example, in certain implementations, a non-robotic device may include one or more engagement portions that are specifically configured to engage with a corresponding engagement portion of a robotic instrument. To illustrate an example, a non-robotic device may include a recess that is keyed to receive a corresponding keyed protrusion provided on a specialized robotic instrument. In such an example, the robotic instrument may be locked into place with respect to the non-robotic device when the keyed protrusion provided of robotic instrument is inserted within the keyed recess of the non-robotic device. In certain alternative implementations, a keyed recess may be provided on the robotic instrument and a corresponding keyed protrusion may be provided on the non-robotic device. Exemplary non-robotic devices will be described further herein.

Figure 3:
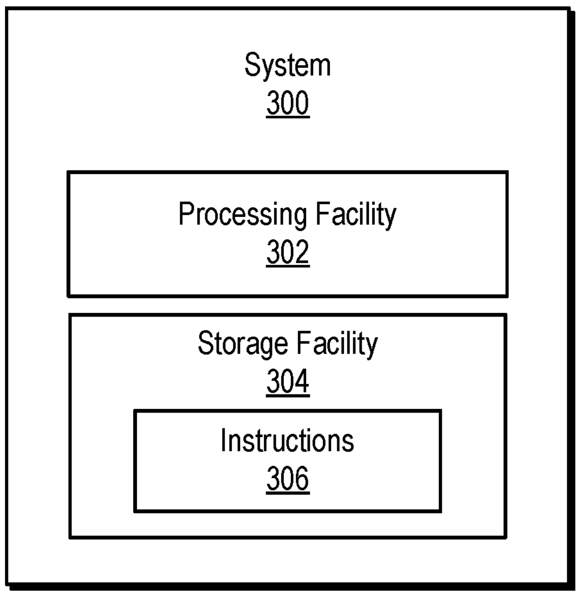
FIG. 3 illustrates an exemplary system configured to facilitate automated operation of a device in a surgical space according to principles described herein.

FIG. 3 illustrates an exemplary system 300 that may be implemented according to principles described herein to facilitate automated operation of a device in a surgical space. As shown, system 300 may include, without limitation, a processing facility 302 and a storage facility 304 selectively and communicatively coupled to one another. Facilities 302 and 304 may each include or be implemented by hardware and/or software components (e.g., processors, memories, communication interfaces, instructions stored in memory for execution by the processors, etc.). In some examples, facilities 302 and 304 may be implemented by a single device (e.g., a single computing device). In certain alternate examples, facilities 302 and 304 may be distributed between multiple devices and/or multiple locations as may serve a particular implementation.

Storage facility 304 may maintain (e.g., store) executable data used by processing facility 302 to perform any of the operations described herein. For example, storage facility 304 may store instructions 306 that may be executed by processing facility 302 to perform any of the operations described herein. Instructions 306 may be implemented by any suitable application, software, code, and/or other executable data instance.

Storage facility 304 may also maintain any data received, generated, managed, used, and/or transmitted by processing facility 302. For example, storage facility 304 may maintain any suitable data associated with facilitating automated operation of a device in a surgical space. Such data may include, but is not limited to, imaging data (e.g., imagery of a surgical space captured by an endoscopic imaging device, a non-robotic imaging device, and/or any other suitable imaging device), data associated with potential objects in a surgical space that a non-robotic device may interact with, three dimensional models of objects that may be located in a surgical space, depth map information associated with a surgical space, pose, position, or orientation information associated with non-robotic devices, robotic instruments, and/or additional objects located in a surgical space, data indicating a procedural context of a surgical session, kinematics data for robotic instruments and/or manipulator arms, data defining guidance content associated with a non-robotic device, user interface content (e.g., graphical objects, notifications, etc.), operating constraint data, operating characteristics data of a device, anatomical characteristics data associated with a surgical space, user input data, and/or any other suitable data.

Processing facility 302 may be configured to perform (e.g., execute instructions 306 stored in storage facility 304) various processing operations associated with facilitating automated operation of a device in a surgical space. For example, processing facility 302 may obtain one or more operating characteristics of a device located in a surgical space; obtain one or more anatomical characteristics associated with the surgical space; and direct a computer-assisted surgical system to automatically perform, based on the one or more operating characteristics of the device and the one or more anatomical characteristics associated with the surgical space, an operation with the device located in the surgical space. These and other operations that may be performed by processing facility 302 are described herein.

At any given time during a surgical procedure associated with a surgical space, it may be desirable to have a computer-assisted surgical system automatically control a device located in the surgical space. To facilitate such automatic control of a device, system 300 (e.g., processing facility 302) may obtain one or more operating characteristics of a device located in a surgical space. As used herein, an "operating characteristic" of a device may include any suitable characteristics associated with operation of a device in a surgical space. For example, operating characteristics may include intrinsic parameters of the device such as operational settings, contact pressure requirements, contact angle requirements, imaging capture parameters (e.g., when the device corresponds to a subsurface imaging device), suctioning parameters (e.g., when the device corresponds to a suctioning device), irrigation parameters (e.g., when the device corresponds to an irrigation device), mode of operation, etc. of the device. Operating characteristics may additionally or alternatively include extrinsic parameters such as position, orientation, pose, sensed forces, etc. of the device in the surgical space.

System 300 may obtain the one or more operating characteristics of a device in any suitable manner. For example, in certain implementations at least some operating characteristics may be accessed from a storage device (e.g., storage facility 304) associated with a computer-assisted surgical system (e.g., surgical system 100). For example, if the device corresponds to a suctioning device, system 300 may access suctioning strength information, information indicating a recommended suctioning distance from tissue, and/or any other suitable information from the storage device. Alternatively, if the device corresponds, for example, to a subsurface imaging device, system 300 may access imaging capture parameters, contact angle requirement information, contact pressure requirement information, operational settings, and/or any other suitable information from the storage device.

Figure 4:
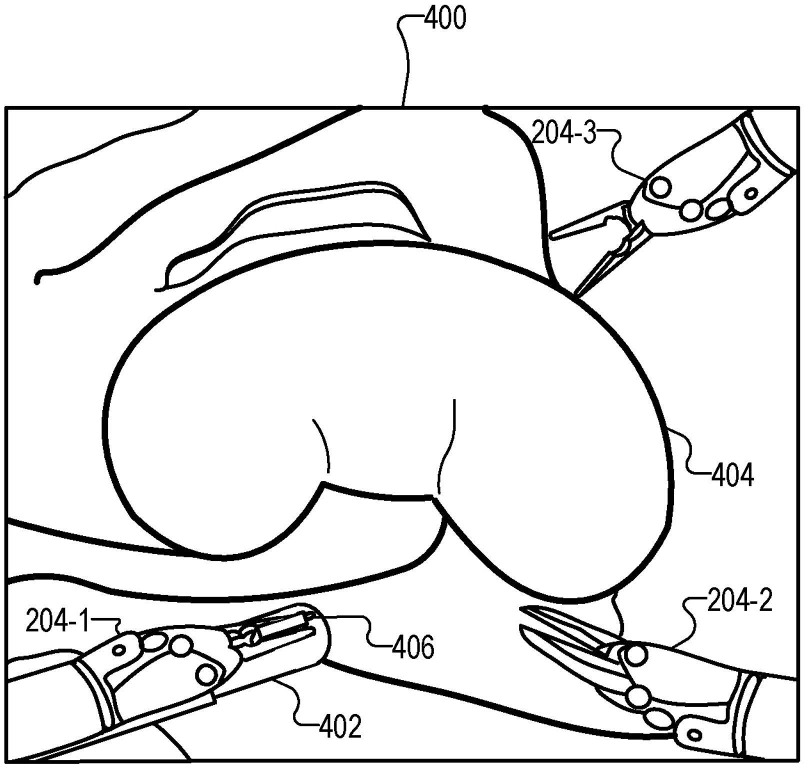
FIGS. 4-7B illustrate exemplary images of a surgical space according to principles described herein.

To illustrate an example, FIG. 4 shows an image 400 of an exemplary non-robotic device that may be automatically operated during a surgical procedure in a surgical space according to principles described herein. As shown in FIG. 4, image 400 illustrates a surgical space in which a non-robotic device 402 and robotic instruments 204-1 through 204-3 are provided in relation to a kidney 404 of a patient (e.g., patient 108). As shown in FIG. 4, non-robotic device 402 includes a protrusion 406 that is grasped by robotic instrument 204-1. As such, movement of robotic instrument 204-1 (e.g., either by a user manipulating master controls of user control system 104 or by automatic operation by surgical system 100) results in movement of non-robotic device 402.

In the example shown in FIG. 4, non-robotic device 402 may be configured to perform or facilitate performance of a surgical procedure with respect to kidney 404. Accordingly, the one or more operating characteristics accessed by system 300 associated with non-robotic device 402 may include a 3D model of non-robotic device 402, information specifying the configuration of protrusion 406, operational settings of non-robotic device 402, optimal pose information of non-robotic device 402 with respect to kidney 404, etc.

Additionally or alternatively, system 300 may obtain the one or more operating characteristics of a device by determining (e.g., detecting, deriving, etc.) the one or more operating characteristics. For example, system 300 may determine, in any suitable manner such as described herein, a position, an orientation, or a pose of a device (e.g., a non-robotic device) in the surgical space. As used herein, a "pose" of an object such as a non-robotic device refers to the combination of the position of the object and the orientation of the object in a space such as a surgical space. The pose may be referred to as a six-dimension (6D) pose because there are three degrees of freedom associated with the position of an object and three degrees of freedom associated with the orientation of the object.

System 300 may determine the pose of a device in any suitable manner. For example, as will be described herein, a device may be engaged by (e.g., grasped by) a robotic instrument. Accordingly, the pose of a device may be determined based on kinematics information associated with the robotic instrument engaging the non-robotic device. Additionally or alternatively, the pose of a device may be determined based on depth data, image data, a determined orientation of the robotic instrument, and/or some combination thereof.

In addition to obtaining operating characteristics of a device, system 300 may obtain one or more anatomical characteristics associated with a surgical space. As described herein, an "anatomical characteristic" may include any information associated with anatomy in a surgical space that may facilitate automatically performing an operation with a device in the surgical space. For example, anatomical characteristics may include, but are not limited to, depth map data of a surgical space, surface contour data of objects (e.g., anatomy, devices, objects, etc.) in the surgical space, data identifying a determined type of tissue in the surgical space, data identifying 3D positions of tissue, etc.

System 300 may obtain one or more anatomical characteristics associated with a surgical space in any suitable manner. In certain implementations, system 300 may derive anatomical characteristics based on one or more data streams associated with a surgical space. For example, system 300 may access, in any suitable manner, one or more data streams that are configured to provide imaging data, kinematics data, procedural context data, system event data, user input data, and/or any other suitable data associated with the surgical space. Based on the information included in the one or more data streams, system 300 may derive one or more anatomical characteristics. For example, system 300 may use depth imagery captured by an imaging device (e.g., imaging device 202) to derive an anatomical characteristic in the form of a depth map of anatomy in the surgical space. Additionally or alternatively, system 300 may use imagery and/or any other suitable information associated with the surgical space to derive anatomical characteristics in the form of surface contour data, 3D tissue position data, and/or any other suitable data associated with anatomy in the surgical space.

In certain examples, system 300 may obtain one or more anatomical characteristics associated with an object in a surgical space to facilitate automatic operation of a device in the surgical space. As used herein, an "object" located in a surgical space may include any anatomy (e.g., tissue, bone, etc.) that may be in a surgical space. In certain examples, an object may correspond to any object in a surgical space that may be the subject of a surgical procedure to be performed in a surgical space. For example, an object may be the subject of a measurement procedure, a diagnostic procedure, an imaging procedure (e.g., a subsurface imaging procedure), a suturing procedure, a tissue tensioning procedure, a cutting procedure, a suction procedure, an irrigation procedure, a therapeutic procedure, and/or any other suitable procedure that may be performed in a surgical space.

In certain examples, an anatomical characteristic associated with a surgical space may be derived, at least in part, based on a procedural context associated with the surgical space. Accordingly, in certain examples, system 300 may be configured to determine a procedural context associated with a surgical space. System 300 may determine the procedural context associated with a surgical space based on any suitable information or combination of information associated with the surgical space. For example, system 300 may detect the procedural context based on one or more images of the surgical space, user input indicating procedural context, a configuration of one or more robotic instruments (e.g., robotic instruments 204) located within the surgical space, a type of device or non-robotic device in the surgical space, kinematics of one or more robotic instruments, and/or any other suitable information. To illustrate an example, based on the presence of non-robotic device 402 in relation to kidney 404 in FIG. 4, system 300 may determine that the procedural context associated with the surgical space in image 400 is associated with an imaging procedure to be performed with respect to kidney 404 using non-robotic device 402.

In certain examples, based on one or more operating characteristics of a device and one or more anatomical characteristics associated with the surgical space, system 300 may apply an operating constraint to the device located in the surgical space. As used herein, an "operating constraint" may include any suitable limit or restriction on use or operation of a device in a surgical space. In certain examples, an operating constraint may be associated with constraining movement of a device in a surgical space. For example, an operating constraint may limit movement of the device within the surgical space to a predefined area or along a predefined motion path. Additionally or alternatively, in certain examples, an operating constraint may include maintaining a position and/or orientation of a device with respect to anatomy and/or another object in a surgical space. To illustrate an example, if a device in a surgical space corresponds to a suctioning device, an operating constraint may include system 300 limiting the distance of the suctioning device from tissue in the surgical space, the angle that the suctioning device is oriented with respect to tissue, the distance of the suctioning device from other objects and/or instruments in the surgical space, and/or any other suitable limit on the position and/or orientation of the suctioning device.

In certain examples, an operating constraint may additionally or alternatively limit and/or restrict use and/or operation of a device in a surgical space by a user. An operating constraint may limit and/or restrict a user from using and/or operating a device in any suitable manner as may serve a particular implementation. For example, an operating constraint may prevent a user from moving and/or orienting a device in a particular manner in the surgical space. To illustrate an example, the device may have a contact angle requirement with respect to tissue in the surgical space. In such an example, the operating constraint may either prevent the user from changing the contact angle of the device with respect to tissue or may prevent the user from adjusting the contact angle outside of some predefined range of acceptable contact angles with respect to the tissue. To illustrate another example, the device may have a distance from tissue requirement that defines a minimum distance that the device may be positioned from tissue to operate properly. In such an example, the operating constraint may prevent a user from moving the device closer to the tissue than the minimum distance indicated by the distance from tissue requirement. To illustrate another example, the device may have a contact pressure requirement that defines a range of acceptable contact pressures for the device to maintain with respect to tissue in the surgical space to operate properly. In such an example, the operating constraint may prevent the user from moving the device in any manner that would result in a contact pressure between the device and the tissue that is outside of the range of acceptable contact pressures.

Additionally or alternatively, an operating constraint may include a limit on an operating parameter of a device in a surgical space. For example, if the device corresponds to a suctioning device, an operating constraint may include limiting the amount of suction provided by way of the suctioning device. If, on the other hand, the device corresponds to an irrigation device, an operating constraint may include limiting an amount of fluid provided through the irrigation device.

In certain examples, system 300 may apply a plurality of operating constraints to a device located in a surgical space. For example, system 300 may apply a first operating constraint to the device that limits movement of the device within the surgical space to a defined area, a second operating constraint that limits the position and/or orientation of the device within the surgical space, and a third operating constraint that limits an operating parameter of the device during a surgical procedure.

In certain examples, system 300 may continuously monitor a surgical space and update one or more operating constraints applied to a device during the course of a surgical procedure. For example, based on one or more operating characteristics of the device and the one or more anatomical characteristics associated with the surgical space, system 300 may apply a first operating constraint to a device that includes the device maintaining a first orientation while the device is at a first position in the surgical space. During the course of the surgical procedure, the device may move from the first position to a second position in the surgical space. Based on the movement of the device from the first position to the second position, system 300 may obtain one or more updated operating characteristics of the device and/or one or more updated anatomical characteristics associated with the surgical space. Based on the one or more updated operating characteristics of the device and/or the one or more updated anatomical characteristics, system 300 may apply an updated operating constraint to the device such that the device maintains a second orientation while the device is in the second position in the surgical space.

Based on one or more operating characteristics of a device, one or more anatomical characteristics associated with the surgical space, and/or optionally an operating constraint applied to a device, system 300 may direct a computer-assisted surgical system (e.g., surgical system 100) to automatically perform an operation with the device located in the surgical space. As used herein, an "operation" that may be performed with a device may include any action and/or use of the device in the surgical space that may facilitate performance of a surgical procedure.

System 300 may direct a computer-assisted surgical system to automatically perform any suitable operation with a device in a surgical space as may serve a particular implementation. For example, system 300 may direct a computer-assisted surgical system to automatically move a device in a surgical space. In such examples, the device may be directly or indirectly (e.g., as a drop-in instrument) attached to a manipulator arm of the computer-assisted surgical system. In certain implementations, system 300 may direct a computer-assisted surgical system to automatically change a pose of a device from a first pose to a second pose in the surgical space. In such examples, system 300 may also direct the computer-assisted surgical system to maintain the device in the second pose during at least part of a surgical procedure in the surgical space.

System 300 may direct a computer-assisted surgical system to automatically perform an operation with a device at any suitable time and based on any surgical context associated with a surgical space. For example, in certain implementations, system 300 may direct a computer-assisted surgical system to automatically perform an operation with a device while a user bimanually controls robotic instruments in a surgical space. To illustrate, during an imaging procedure performed in a surgical space, a user (e.g., surgeon 110-1) may bimanually control only two robotic instruments at a time by manipulating master controls of user control system 104. A non-robotic imaging device may be engaged by (e.g., grasped by) a third robotic instrument. In such examples, for the user to manually teleoperate the non-robotic imaging device, the user would have to switch from controlling at least one of the other robotic instruments to controlling the third robotic instrument that is engaged with the non-robotic imaging device. This undesirably segments the imaging procedure into an imaging phase and a bimanual execution phase, which results in inefficiencies in performance of the imaging procedure. To avoid such segmentation of the imaging procedure, system 300 may direct the computer-assisted surgical system to automatically perform an operation with the non-robotic imaging device. For example, system 300 may direct the computer-assisted surgical system to automatically move the non-robotic imaging device within the surgical space and/or automatically use the non-robotic imaging device to capture imagery within the surgical space while the user is able to bimanually operate two robotic instruments other than the third robotic instrument that is engaged with and automatically manipulating the non-robotic imaging device. This may allow the user to bimanually teleoperate the two non-robotic instruments while referring to live interoperative image guidance provided based on the automated operation of the non-robotic imaging device.

In certain examples, system 300 may direct a computer-assisted surgical system to automatically generate a motion path for a device to follow in a surgical space. Such a motion path may be generated in any suitable manner. For example, system 300 may analyze image 400 shown in FIG. 4 and determine, based on image 400, anatomical characteristics of kidney 404, characteristics of non-robotic device 402, and/or any other suitable characteristics associated with the surgical space, that a procedural context is associated with a non-robotic imaging device capturing imagery of kidney 404. Based on such a procedural context, system 300 may automatically generate a motion path for non-robotic device 402 to automatically follow, without requiring that the user provide further input.

Figure 5:
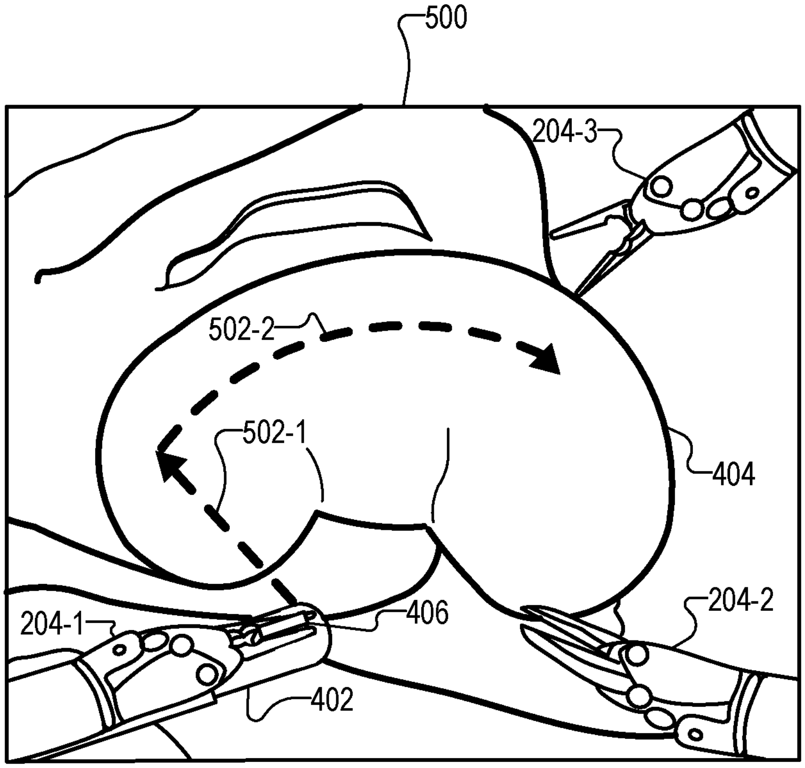

To illustrate an example, FIG. 5 shows an exemplary image 500 of a surgical space in which non-robotic device 402 and robotic instruments 204-1 through 204-3 are provided in relation to kidney 404 of a patient (e.g., patient 108). As shown in FIG. 5, image 500 also includes a plurality of motion paths 502 (e.g., motion path 502-1 and motion path 502-2) that robotic instrument 204-1 may automatically follow to facilitate performance of a surgical procedure in the surgical space. In the example shown in FIG. 5, system 300 may direct a computer-assisted surgical system to automatically move robotic instrument 204-1 so that the grasped non-robotic device 402 moves along motion path 502-1 to contact a surface of kidney 404. After robotic instrument 204-1 is moved along motion path 502-1 and the grasped non-robotic device 402 contacts the surface of kidney 404, system 300 may direct the computer-assisted surgical system to automatically move robotic instrument 204-1 and grasped non-robotic device 402 along motion path 502-2 such that non-robotic device 402 follows the surface of kidney 404.

In the example shown in FIG. 5, motion paths 502 are provided for display within image 500. Accordingly, a user may be able to visualize one or more motion paths that a device may automatically follow within a surgical space prior to the device following the motion paths. However, it is understood that in certain alternative examples motion paths such as motion paths 502 may not be provided for display to a user. In such examples, the user may see, for example, robotic instrument 204-1 and the grasped non-robotic device 402 automatically moving within the surgical space without a graphical object representative of the motion paths being provided for display.

In certain implementations, system 300 may direct a computer-assisted surgical system to automatically move a device in a surgical space based on movement of a robotic instrument attached to the computer-assisted surgical system. In such examples, the robotic instrument may be different than the robotic instrument that is engaged with (e.g., that is grasping) the device. For example, while a user teleoperates one or more of robotic instruments 204-2 and 204-3 shown in FIG. 4, system 300 may automatically move robotic instrument 204-1 and non-robotic device 402 based on movement of one or more of robotic instruments 204-2 and 204-3. To illustrate an example, system 300 may direct a computer-assisted surgical system to automatically control robotic instrument 204-1 such that non-robotic device 402 follows robotic instrument 204-2 wherever robotic instrument 204-2 moves within the surgical space.

In certain examples, system 300 may facilitate a user teleoperating a robotic instrument to trace a motion path for a device to automatically follow within the surgical space. For example, system 300 may facilitate a user teleoperating robotic instrument 204-2 to trace a motion path for non-robotic device 402 to follow with respect to kidney 404. Based on the motion path traced by robotic instrument 204-2, system 300 may direct the computer-assisted surgical system to automatically move robotic instrument 204-1 in any suitable manner such that non-robotic device 402 follows the motion path. For example, robotic instrument 204-1 may automatically move along the motion path in real time as a user traces the motion path with robotic instrument 204-2. Alternatively, robotic instrument 204-1 may automatically move along the motion path after the user has completed tracing the motion path in the surgical space.

To illustrate another example, the surgical context associated with image 400 shown in FIG. 4 may include a cutting procedure in which a user teleoperates robotic instrument 204-2 to cut tissue located in the surgical space. In such an example, non-robotic device 402 may correspond to a suctioning device that is used to suction content (e.g., blood, cut tissue, etc.) in the surgical space. During the cutting procedure, system 300 may instruct a computer-assisted surgical system to automatically control robotic instrument 204-1 to move the suctioning device in relation to a cutting trajectory of robotic instrument 204-2 to optimally suction the content during the cutting procedure. In addition, system 300 may direct the computer-assisted surgical system to automatically adjust an operating parameter of the suctioning device. For example, during the cutting procedure, system 300 may analyze the surgical space in real time and determine, in any suitable manner, that there has been an increase in blood entering the surgical space due to the cutting procedure. In such an example, system 300 may direct the computer-assisted surgical system to automatically increase the suction strength of the suctioning device to facilitate removal of the blood. In so doing, it is possible to increase the ease of use and efficiency of a computer-assisted surgical system because the user does not have to worry about adjusting the operating parameters of the device and/or switching between manually teleoperating robotic instruments 204 during a surgical procedure.

Figure 6:
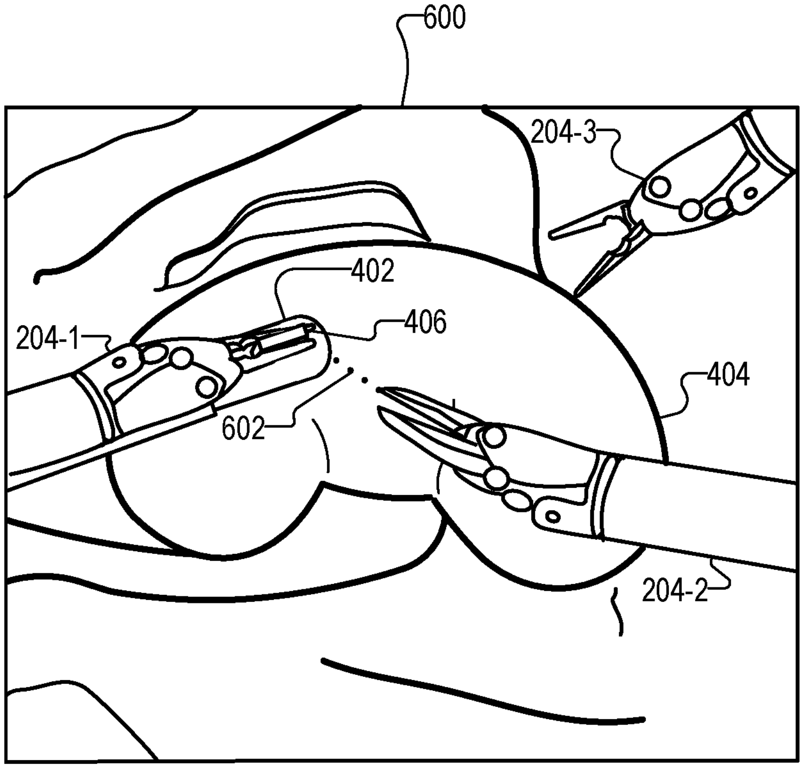

In certain examples, system 300 may direct a computer-assisted surgical system to automatically maintain a device at a rigid offset (e.g., a rigid Euclidean offset) with respect to a robotic instrument to which the device is not attached. Such a rigid offset may include any suitable distance between the device and the robotic instrument as may serve a particular implementation. To illustrate an example, FIG. 6 shows an exemplary image 600 of a surgical space in which robotic instruments 204-1 through 204-3 are provided in relation to kidney 404. In the example shown in FIG. 6, non-robotic device 402 is provided at a rigid offset 602 away from robotic instrument 204-2. As such, whenever robotic instrument 204-2 moves within the surgical space, system 300 directs the computer-assisted surgical system to automatically move robotic instrument 204-1 so that non-robotic device 402 stays at rigid offset 602 with respect to robotic instrument 204-2.

In certain examples, system 300 may additionally or alternatively direct the computer-assisted surgical system to automatically maintain a device at a predefined orientation within the surgical space while automatically maintaining a rigid offset. For example, robotic instrument 204-1 and non-robotic device 402 may maintain the same orientation shown in FIG. 6 and the same distance from robotic instrument 204-2 indicated by rigid offset 602 regardless of where robotic instrument 204-2 is moved within the surgical space.

In certain alternative examples, system 300 may direct a computer-assisted surgical system to automatically adjust the orientation of a device while maintaining a rigid offset with respect to a robotic instrument. For example, while a user manually teleoperates robotic instrument 204-2, system 300 may maintain rigid offset 602 but may adjust the orientation of non-robotic device to facilitate the user performing a surgical procedure with respect to kidney 404.

In certain examples, system 300 may direct a computer-assisted surgical system to automatically perform an operation to maintain a state of contact of a device with respect to a surface of an object in a surgical space. System 300 may facilitate a device maintaining a state of contact with respect to a surface of an object in any suitable manner. For example, system 300 may determine, based on one or more anatomical characteristics associated with a surgical space, that there will be a change in at least one of a contact pressure or a contact angle of a device with respect to an object as the device moves along the surface of the object. In response to the determination that there will be a change in at least one of the contact pressure or the contact angle, system 300 may direct the computer-assisted surgical system to automatically move the device such that the device maintains at least one of a predefined amount of contact pressure or the contact angle of the device with respect to the object while the device moves along the surface of the object.

To illustrate an example, non-robotic device 402 shown in FIG. 4 may correspond to a drop-in ultrasound probe that is configured to contact a surface of kidney 404 to capture ultrasound imagery of kidney 404. With ultrasound imaging, the quality of a captured ultrasound image depends on the amount of pressure that a drop-in ultrasound probe is pushed into tissue such as kidney 404. Too much pressure may negatively affect the quality of a captured ultrasound image. Similarly, not enough pressure may also negatively affect the quality of an ultrasound image. Accordingly, in such examples, system 300 may direct a computer-assisted surgical system to automatically control robotic instrument 204-1 so as to maintain a state of contact of non-robotic device 402 with respect to kidney 404.

The state of contact between a non-robotic imaging device and an object in a surgical space may include one of a full contact state, a partial contact state, or a no contact state. System 300 may be configured to determine a state of contact between a non-robotic imaging device and an object in a surgical space in any suitable manner. For example, in certain implementations, system 300 may monitor signal strength and/or other attributes of an image captured by a non-robotic imaging device to determine a state of contact. In certain examples, the signal strength of a captured image may be represented by image content in the captured image. Accordingly, in certain examples, system 300 may monitor the image content in imagery captured by a non-robotic imaging device to determine a state of contact of a non-robotic imaging device with respect to a surface of an object.

System 300 may monitor the image content in imagery captured by a non-robotic imaging device in any suitable manner. For example, system 300 may determine an amount of image content in a given image to determine a contact state of a non-robotic imaging device. If the amount of image content is above a predefined threshold, system 300 may determine that the contact state between the non-robotic imaging device and the tissue is acceptable. To illustrate, an image captured by the non-robotic imaging device may include a first region that includes image content (e.g., an image of a surface of a kidney) and a second region that does not include image content (e.g., a black region that represents air space adjacent to the kidney). System 300 may be configured to process such an image in any suitable manner and determine that the non-robotic imaging device is in substantially a full contact state if an area associated with the first region is above some predefined threshold. Alternatively, system 300 determine that the non-robotic imaging device is in a partial contact state if the area associated with the first region is below some predefined threshold.

Figure 7A:
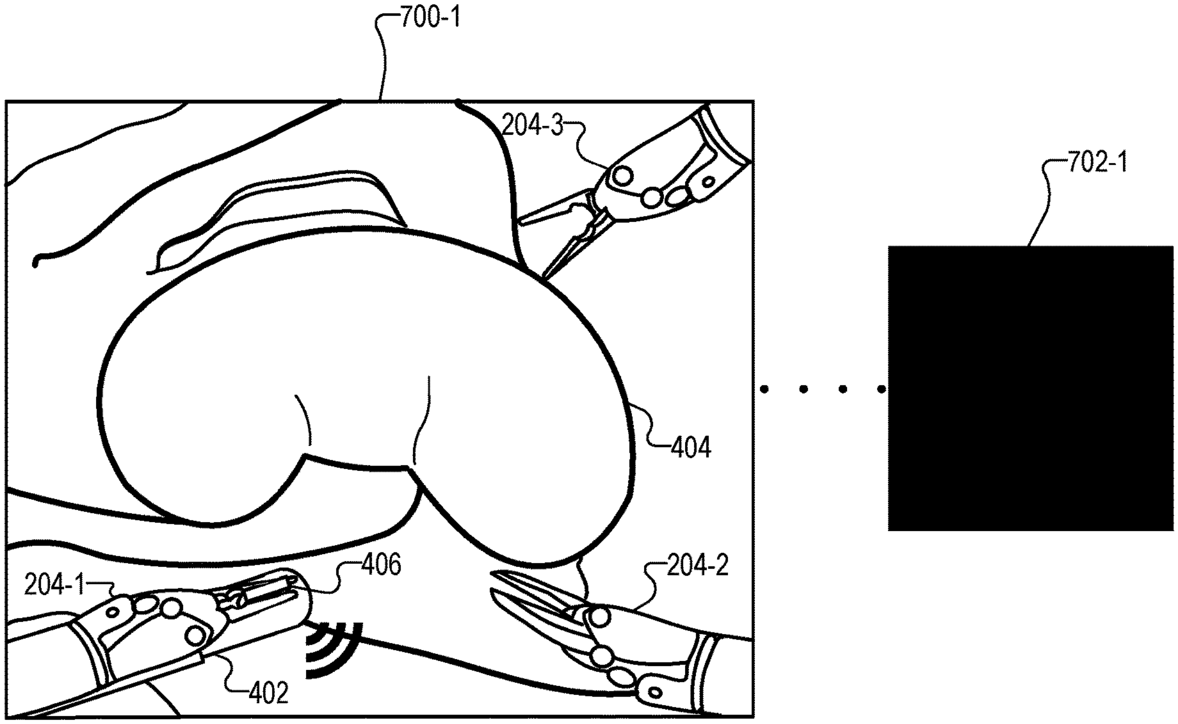
Figure 7B:
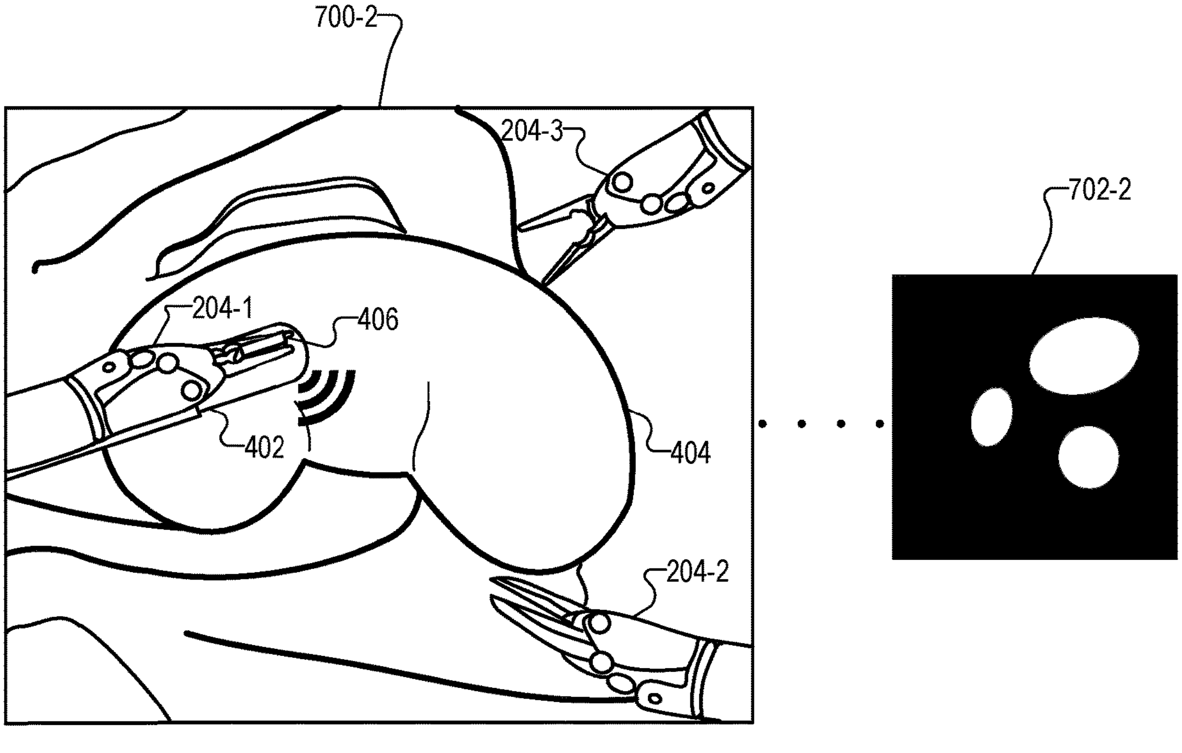

In certain alternative examples, system 300 may compare an amount of image content in a previous image to an amount of image content in a current image captured by a non-robotic imaging device to determine the contact state of a non-robotic imaging device with respect to an object in a surgical space. To illustrate, FIGS. 7A and 7B show images 700 (e.g., images 700-1 and 700-2) of a surgical space in which non-robotic imaging instrument 402 is being used to capture ultrasound images 702 (e.g., ultrasound images 702-1 and 702-2) at different positions within the surgical space. As shown in FIG. 7A, non-robotic device 402 is positioned away from (i.e., not in contact with) kidney 404. As such, ultrasound image 702-1 is blank and does not include any subsurface image of kidney 404. On the other hand, in FIG. 7B, non-robotic device 402 is positioned near kidney 404 such that ultrasound image 702-2 includes a subsurface image of kidney 404. The change in image content between ultrasound image 702-1 and 702-2 may indicate that non-robotic device is in contact with kidney 404 when ultrasound image 702-2 is captured. This is one example of how image content may be determined and used. Other suitable ways of determining and using image content may be used in other examples.

Ultrasound images 702 are shown to the side of images 700 in FIGS. 7A and 7B for illustrative purposes. It is understood that ultrasound images 702 may be provided for display in any suitable manner as may serve a particular implementation. In certain examples, ultrasound images may be provided as an augmentation to an image of a surgical space (e.g., as an overlay over an endoscopic image of a surgical space). For example, ultrasound image 702-1 may be overlaid over a portion of image 700-2 in certain implementations so that a user (e.g., surgeon 110-1) may view the captured ultrasound imagery concurrently and in place while teleoperating non-robotic device 402. Additionally or alternatively, ultrasound images 700 may be provided for display at any other location relative to an image of a surgical space and/or by way of any other suitable display device (e.g., display monitor 114) associated with a computer-assisted surgical system.

Depending on the state of contact of a non-robotic device with respect to an object, system 300 may direct a computer-assisted surgical system to automatically perform an operation with respect to the non-robotic device. For example, system 300 may direct a computer-assisted surgical system to automatically move a non-robotic imaging device such that the non-robotic imaging device maintains a full contact state with respect to an object in a surgical space.

In certain implementations, system 300 may direct a computer-assisted surgical system to automatically adjust a pose of device to improve performance of a surgical procedure. For example, system 300 may perform an image-based visual servoing operation to improve image quality. As part of such an image-based visual servoing operation, system 300 may direct a computer-assisted surgical system to automatically make adjustments to the pose of a non-robotic imaging device. Such an image-based visual servoing operation may help ensure that a non-robotic imaging device such as a drop-in ultrasound probe maintains a desired position and/or orientation with respect to an object in the surgical space. In certain examples, the maintaining of a desired position and/or orientation may include maintaining an amount of pressure and/or a desired contact angle with respect to an object in a surgical space (e.g., to capture adequate imagery).

Figure 8:
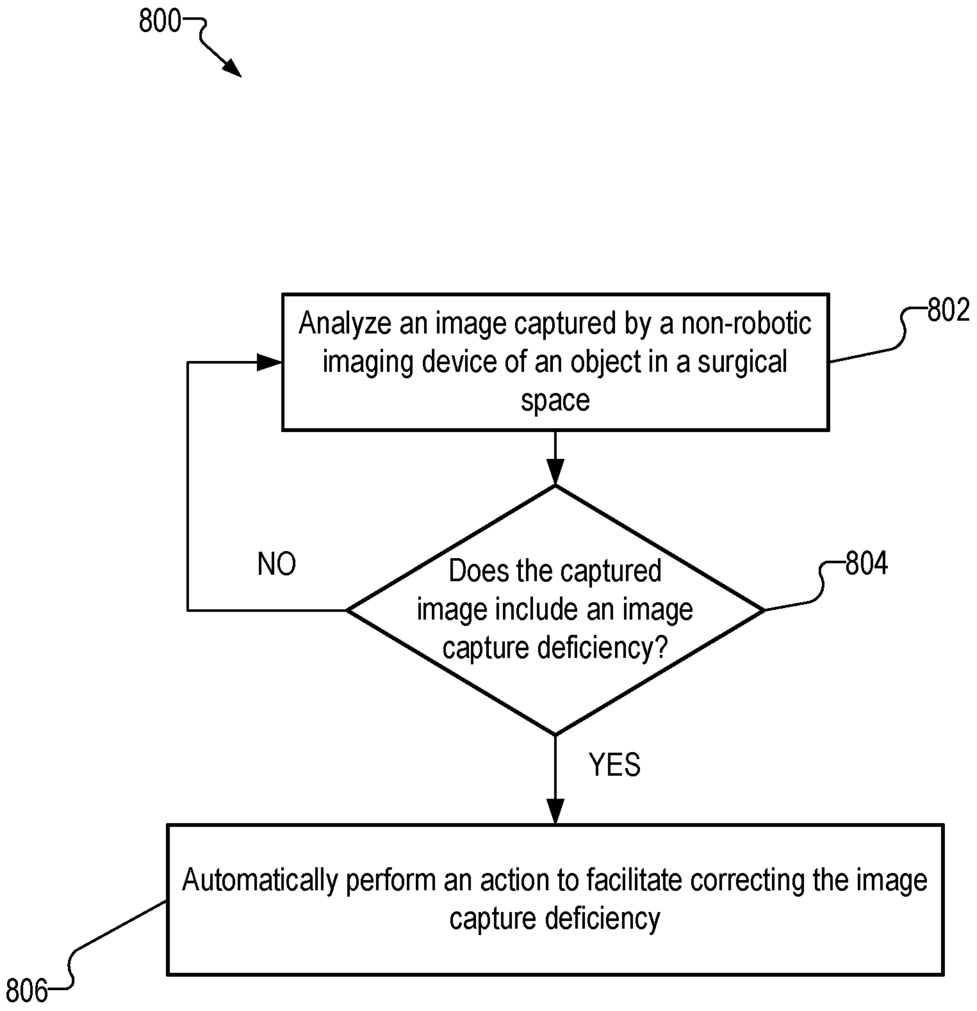
FIG. 8 illustrates an exemplary flow chart depicting various operations that may be performed by the system illustrated in FIG. 3 according to principles described herein.

A computer-assisted surgical system may perform an image-based visual servoing operation in any suitable manner. To illustrate, FIG. 8 shows a flow diagram 800 with exemplary operations that may be performed by system 300 when performing an image-based visual servoing operation in certain implementations. In operation 802, system 300 may analyze an image captured by a non-robotic imaging device of an object in a surgical space. System 300 may analyze the captured image in any suitable manner. For example, system 300 may use any suitable image processing technique to analyze the captured image.

In operation 804, system 300 may determine whether the captured image includes an image capture deficiency. An image capture deficiency may correspond to any suboptimal attribute of an image captured by a non-robotic imaging device. For example, in implementations where a non-robotic imaging device corresponds to a drop-in ultrasound probe, a particular contact state of the non-robotic imaging device with respect to an object (e.g., tissue such as a kidney) may result in an image capture deficiency. For example, a no contact state or a partial contact state of the non-robotic imaging device with respect to an object may cause an image capture deficiency. Additionally or alternatively, too much pressure of the drop-in ultrasound probe into an object (e.g., tissue such as a kidney) may cause an image capture deficiency. Additionally or alternatively, not enough pressure of the drop-in ultrasound probe into the object may cause an image capture deficiency. In such examples, the image content of the captured image may indicate that there is not enough contact, too much surface contact pressure, not enough surface contact pressure, or a suitable amount of surface contact pressure of the drop-in ultrasound probe with respect to the object. Accordingly, in certain implementations, system 300 may determine that there is an image capture deficiency based on an amount of image content in a captured image.

System 300 may determine whether a captured image includes an image capture deficiency in any suitable manner. For example, in instances where the image capture deficiency is associated with a partial contact state, system 300 may perform any suitable imaging processing operation to detect image velocity vectors in the captured image. Such image velocity vectors may indicate a boundary between an object (e.g., a tissue wall) and air space adjacent to the object. The larger the image velocity vectors, the less the non-robotic imaging device may be in contact with the object. As such, image velocity vectors may be used to determine whether a captured image includes image capture deficiency due to a partial contact state.

If the answer to operation 804 is "NO", system 300 may return to operation 802 and analyze an additional image of an object captured by the non-robotic imaging device. However, if the answer in operation 804 is "YES", system 300 may direct a computer-assisted surgical system to automatically perform an action to facilitate correcting the image capture deficiency in operation 806.

System 300 may direct a computer-assisted surgical system to perform any suitable action to facilitate correcting an image capture deficiency as may serve a particular implementation. In certain examples, the automatically performing of the action in operation 806 may include system 300 directing a computer-assisted surgical system to automatically adjust a pose of a non-robotic device during a surgical procedure. For example, in operation 806, system 300 may automatically adjust at least one of a position or an orientation of a non-robotic device. To illustrate, when a non-robotic imaging device is in a partial contact state with respect an object in a surgical space, system 300 may perform a closed-loop feedback operation in which system 300 uses detected image velocity vectors in a captured image to automatically adjust at least one of a position or an orientation of a non-robotic imaging device. For example, system 300 may perform any suitable image processing operation to detect image velocity vectors in a captured image. Based on the image velocity vectors, system 300 may direct a computer-assisted surgical system to automatically move the non-robotic imaging device in a direction with respect to an object that would result in the non-robotic imaging device more fully contacting the object. After movement of the non-robotic imaging device, system 300 may detect additional image velocity vectors in an additional captured image and direct the computer-assisted surgical system to automatically move the non-robotic imaging device again based on the additional image velocity vectors to further increase the amount of contact of the non-robotic imaging device with respect to the object. System 300 may automatically repeat such operations any suitable number of times so as to minimize the image velocity vectors and ensure that the non-robotic imaging device maintains an acceptable amount of contact with respect to the object.

In certain implementations, a device may require a specific angle of contact with an object in a surgical space to provide reliable measurements. For example, a non-robotic imaging device may require maintaining tissue contact along a surface normal (e.g., within a threshold tolerance of 90° with respect to the surface) with respect to a surface of an object to provide suitable subsurface imaging. In addition, maintaining tissue contact along a surface normal may provide information regarding an angular offset of a captured image with respect to subsurface anatomical structures. However, contact of a non-robotic imaging device with respect to a surface of an object at an angle other than a surface normal may result in such information not being available and, as such, may result in an image capture deficiency in certain implementations. Accordingly, in certain examples, system 300 may additionally or alternatively direct a computer-assisted surgical system to automatically adjust a contact angle of a device with respect to an object during a surgical procedure.

Figure 9:
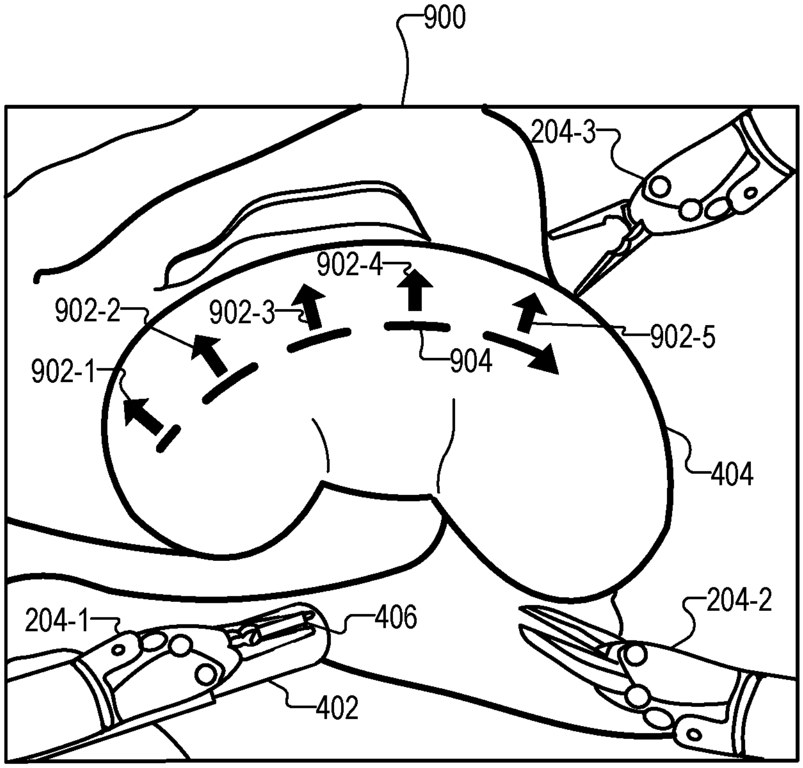
FIG. 9 illustrates an additional exemplary image of a surgical space according to principles described herein.

To illustrate an example, FIG. 9 shows an image 900 of a surgical space in which robotic instruments 204-1 through 204-3 are provided in relation to kidney 404. As shown in FIG. 9, markers 902 (e.g., markers 902-1 through 902-5) are provided for illustrative purposes to depict a surface normal with respect to a particular portion of the surface of kidney 404 associated with each marker 902 along a motion path 904.

System 300 may determine the surface normal of an object in a surgical space in any suitable manner. For example, system 300 may determine the surface normal based on depth data (e.g., a depth map) associated with a surgical space. Additionally or alternatively, system 300 may determine the surface normal associated with each marker (e.g., markers 902) based on a 3D model of an object to be imaged. For example, in FIG. 9, a 3D model of kidney 404 may be used in certain implementations to determine the surface normal of any given portion of the surface of kidney 404. At each marker 902 shown in FIG. 9, system 300 may direct a computer-assisted surgical system to automatically update the orientation of non-robotic device 402 to adjust the contact angle of non-robotic device 402 with respect to the surface of kidney 404.

Based on markers 902, system 300 may direct a computer-assisted surgical system to automatically control the movement trajectory and the contact angle of non-robotic device 402 as non-robotic device 402 moves along motion path 904. In so doing it may be possible to improve image quality, simplify the surgical procedure, and/or improve efficiency of a user of a computer-assisted surgical system.

In the example shown in FIG. 9, five markers 902 are shown. However, it is understood that system 300 may direct a computer-assisted surgical system to automatically adjust a contact angle of a device with respect to an object in a surgical space any suitable number of times as may serve a particular implementation.

Figure 10:
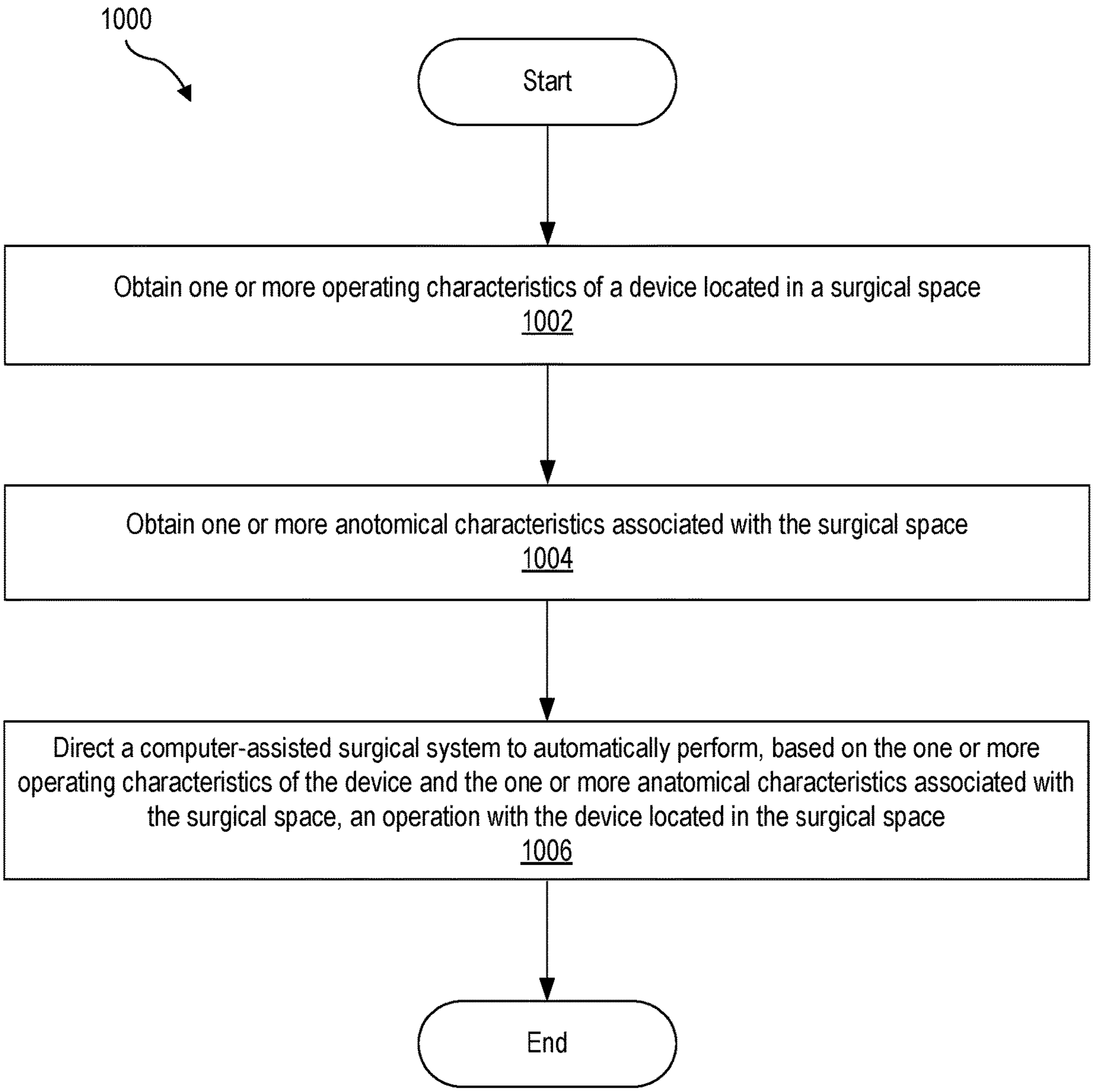
FIG. 10 illustrates an exemplary method for facilitating automated operation of a device in a surgical space according to principles described herein.

FIG. 10 illustrates an exemplary method for facilitating automated operation of an instrument in a surgical space. While FIG. 10 illustrates exemplary operations according to one embodiment, other embodiments may omit, add to, reorder, and/or modify any of the operations shown in FIG. 10. One or more of the operations shown in FIG. 10 may be performed by a system such as system 300, any components included therein, and/or any implementation thereof.

In operation 1002, a processor (e.g., a processor implementing processing facility 302) associated with a computer-assisted surgical system (e.g., surgical system 100) may obtain one or more operating characteristics of a device located in a surgical space. Operation 1002 may be performed in any of the ways described herein.

In operation 1004, the processor may obtain one or more anatomical characteristics associated with the surgical space. Operation 1004 may be performed in any of the ways described herein.

In operation 1006, the processor may direct the computer-assisted surgical system to automatically perform, based on the one or more operating characteristics of the device and the one or more anatomical characteristics associated with the surgical space, an operation with the device located in the surgical space. Operation 1006 may be performed in any of the ways described herein.

Although the preceding disclosure describes operations that facilitate a computer-assisted surgical system automatically operating a device that is, for example, engaged by a robotic instrument, it is understood that system 300 may also perform various operations associated with identification of a target object in a surgical space, identification of a robotic instrument to be used to interact with a target object, facilitating a robotic instrument interacting with (e.g., grasping or otherwise engaging) a target object, and/or facilitating guided teleoperation of a non-robotic device in a surgical space. As used herein, a "target object" may refer to any object that may be located in a surgical space. For example, a target object may correspond to a non-robotic device located in the surgical space, a robotic instrument located within the surgical space, or any other object or instrument that may be located in a surgical space.

To that end, in certain examples, system 300 may be configured to determine whether a target object is located in a surgical space. System 300 may determine whether a target object is located in a surgical space in any suitable manner. For example, in certain implementations, system 300 may use vision-based image processing techniques (e.g., computer vision techniques) to determine whether a target object is located in a surgical space. In such examples, system 300 may be configured to use any suitable vision-based image processing technique to track and identify one or more objects and/or types of objects (e.g., robotic instruments, non-robotic devices, tissue, etc.) within a surgical space. Such vision-based image processing techniques may include system 300 using imaging device 202 to capture imagery (e.g., one or more images) of the surgical space. System 300 may use the captured imagery as input for the vision-based image processing techniques to determine information associated with the objects in the surgical space. For example, system 300 may use the captured imagery to determine, in any suitable manner, whether a target object is located in the surgical space. In addition, system 300 may use the captured imagery and any suitable vision-based image processing technique to determine the size, the shape, the pose, and/or the number of objects located in the surgical space. In certain examples, any object in the surgical space other than a robotic instrument may be considered as a candidate for being identified as a target object located in the surgical space.

Additionally or alternatively, system 300 may be configured to determine whether a target object is located in a surgical space based on a depth map of the surgical space. System 300 may be configured to use a depth map in any suitable manner. For example, system 300 may detect a difference between a current depth map of the surgical space and one or more previous depth maps of the surgical space. Based on the detected difference, system 300 may identify known object shapes, known patterns of object shapes (e.g., insertion patterns), and/or any other suitable information that may be indicative of a target object that is either located in a surgical space and/or that is in the process of being inserted in the surgical space. System 300 may use any suitable number of depth maps to determine whether a target object is located in a surgical space as may serve a particular implementation. In certain examples, system 300 may compare a sequence of previous-frame depth maps to a current-frame depth map to determine whether a target object is located in a surgical space. In certain examples, system 300 may be configured to continually monitor a depth map of a surgical space to determine in real time whether a target object is located in a surgical space.

Exemplary operations that may be performed by system 300 when using a depth map to determine whether a target object is located in a surgical space may include obtaining a depth map of a surgical space. System 300 may obtain the depth map of the surgical space in any suitable manner. For example, system 300 may use imaging device 202 to capture depth data, which system 300 may then use to generate a depth map of the surgical space in any suitable manner. Alternatively, system 300 may receive the depth map from any suitable source.

System 300 may extract a representation of an object from the depth map. A representation of an object may have any suitable format as may serve a particular implementation. For example, a representation of an object may correspond to a surface contour of an object, a volumetric reconstruction of an object (e.g., a point cloud of the object), an outer contour shape of an object, etc. System 300 may extract the representation of the object from the generated depth map in any suitable manner. For example, system 300 may subtract a previous depth map of the surgical space from the current depth map of the surgical space that includes the object. The depth map data that remains after such a subtraction may be representative of the object in the surgical space. As another example, system 300 may segment the depth map by classifying points in the depth map as being associated with particular objects or types of objects. Points that are labeled as corresponding to the object may be extracted as a representation of the object.

System 300 may compare the extracted representation of the object to a plurality of representations of known target objects. This may be accomplished in any suitable manner. For example, system 300 may access data representative of the plurality of known target objects from storage facility 304. System 300 may then compare the extracted representation to at least some of the representations included in the plurality of representations of known target objects. Based on the comparison, system 300 may use any suitable image processing technique to determine a degree of similarity between the extracted representation and at least some of the representations included in the plurality of representations of known target objects. In certain examples, system 300 may compare the extracted representation to each of the representations included in the plurality of representations of known target objects.

System 300 may identify, from the plurality of representations of known target objects, a representation of a known target object that matches the extracted representation of the object. System 300 may determine whether there is a match between the extracted representation of the object and a representation of a known target object in any suitable manner. For example, system 300 may determine that there is a match when a degree of similarity between the extracted representation and a representation of a known target object is above a predefined threshold amount. To illustrate, system 300 may determine that there is a match if the degree of similarity between the extracted representation and the representation of the known target object is above 95%. Such a percentage degree of similarity may be determined in any suitable manner.

In certain alternative implementations, system 300 may use image subtraction to determine whether there is a match between the extracted representation and a representation of a known target object. In such examples, system 300 may obtain image data that corresponds to the depth positions in the extracted representation. System 300 may also obtain image data of the representation of the known target object. System 300 may then subtract pixel values of pixels in the image data of the extracted representation from pixel values of similarly positioned pixels in the image data of the representation of the known target object. When the result of such image subtraction is zero or almost zero, the extracted representation and the representation of a known target object may be considered as being a perfect match. However, system 300 may be configured to determine that there is a match between the extracted representation and the representation of a known target object as long as the subtracted result is within some predefined threshold from zero.

Based on the identified match, system 100 may identify the object as a target object located in the surgical space.

In certain examples, the determination that a target object is located in a surgical space may include system 300 determining what type of target object is located in the surgical space. System 300 may determine the type of the target object located in a surgical space in any suitable manner. For example, system 300 may access an image of a surgical space (e.g., an image captured by imaging device 202).

System 300 may extract an image of a non-robotic device from the captured image. System 300 may extract the image in any suitable manner using any suitable image processing technique. For example, system 300 may use computer vision techniques and image segmentation to locate boundaries (lines, curves, etc.) of the non-robotic device in the captured image to determine a representation of the non-robotic device. In certain examples, such a representation may correspond to an outer contour shape of the non-robotic device and/or any other suitable representation, such as those described herein. An outer contour shape of a target object such as a non-robotic device may define a profile of a perimeter of the target object when viewed from a particular viewpoint within the surgical space. Based on the representation of the non-robotic device, system 300 may extract the image of the non-robotic device from a remainder of the captured image.

System 300 may compare a representation of the non-robotic device to a plurality of representations (e.g., a plurality of outer contour shapes) of a plurality of known non-robotic devices. Each representation included in the plurality of representations of the plurality of known non-robotic devices may represent a different type of non-robotic device. For example, a first representation included in the plurality of representations of known non-robotic devices may be representative of a first type of non-robotic device, the second representation may be representative of a second type of non-robotic device, and the third representation may be representative of a third type of non-robotic device.

System 300 may compare the representation of the non-robotic device to the plurality of representations of a plurality of known non-robotic devices system in any suitable manner. For example, system 300 may compare the representation to the first representation, the second representation, and the third representation that are each included in the plurality of representations of the plurality of known non-robotic devices. Based on the comparison, system 300 may determine, in any suitable manner, a degree of similarity between the representation of the non-robotic device and each of the first, second, and third representations.

From the plurality of representations of the plurality of known target objects, system 300 may select a representation that matches the representation of the non-robotic device. System 300 may determine that the selected representation matches the representation of the non-robotic device in any suitable manner. Continuing with the example described above, system 300 may determine that the degree of similarity between the representation of the non-robotic device and the third representation is relatively higher than the degree of similarity between the representation of the non-robotic device and the first and second representations. Accordingly, system 300 may select the third representation as matching the representation of the non-robotic device.

System 300 may determine the type of the non-robotic device based on the selected matching representation. This may be accomplished in any suitable manner. For example, continuing with the example described above, system 300 may determine that the type of the non-robotic device corresponds to the type of non-robotic device represented by the third representation included in the plurality of representations of known non-robotic devices.

In certain alternative examples, system 300 may be configured to determine that a target object is located in a surgical space based on information provided by a user of surgical system 100. For example, assistant 110-2, nurse 110-3, and/or any other individual associated with a surgical procedure may place a target object within a surgical space and then enter information, in any suitable manner, that indicates that the target object is in the surgical space. In certain examples, such information may also indicate the type of target object, an insertion location of the target object, and/or any other suitable information associated with the target object.

In certain examples, system 300 may be configured to provide a notification to a user (e.g., surgeon 110-1) indicating that a target object has been detected in a surgical space and/or providing any suitable information to the user to facilitate an intended interaction (e.g., a grasping interaction) with the target object. System 300 may provide such a notification in any suitable manner. For example, system 300 may provide a text-based notification in an interface displayed by way of the stereoscopic image viewer of user control console 104. Such a text-based notification may inform the user that a target object has been detected in the surgical space and may provide any other suitable information associated with the target object. Additionally or alternatively, system 300 may be configured to provide any suitable audible notification indicating that a target object has been detected in a surgical space. For example, an exemplary audible notification may include system 300 playing an audio clip with the expression "An ultrasound probe has been inserted."

In certain examples, system 300 may be configured to detect an intent of a user of a computer-assisted surgical system to use a robotic instrument attached to the computer-assisted surgical system to interact with the target object while the target object is located in the surgical space. System 300 may detect the intent of the user to interact with a target object in any suitable manner. In certain examples, system 300 may provide a notification to the user prompting the user to indicate whether the user intends to interact with a target object. For example, system 300 may provide a notification, in any suitable manner, to the user indicating that a target object has been detected in the surgical space Such a notification may also inquire, in any suitable manner, whether the user intends to interact with the target object. System 300 may then detect any suitable user input that may be provided by the user to indicate the intent of the user to interact with a target object.

For example, system 300 may detect the intent of the user to interact with a target object by detecting a voice-based command provided by a user (e.g., surgeon 110-1, assistant 110-2, etc.) of surgical system 100. System 300 may detect a voice-based command in any suitable manner using any suitable speech recognition algorithm. In certain examples, system 300 may store (e.g., through storage facility 304) one or more predefined voice-based commands that are configured to cause system 300 to determine that the user intends to interact with a target object. For example, the expressions "I want to use ultrasound," "pick up ultrasound probe," etc.

may correspond to exemplary pre-defined voice-based commands that system 300 may be configured to use to determine the intent of the user to interact with a target object that corresponds to a drop-in ultrasound probe.

Additionally or alternatively, system 300 may detect a gesture-based command provided by a user of the computer-assisted surgical system. Such a gesture-based command may include any suitable input (that may be provided by way of any suitable user interface associated with surgical system 100. For example, system 300 may detect a gesture-based command provided by way of surgeon 110-1 manipulating master controls of user control system 104 (e.g., one or more commands that cause a robotic instrument to move toward and/or within a threshold distance of the target object). Additionally or alternatively, system 300 may detect a gesture-based command provided by way of an input (e.g., a touch input, a mouse cursor input, etc.) with respect to display monitor 114 or any other device that may be communicatively coupled to surgical system 100.

In certain examples, system 300 may detect the intent of a user to interact with a target object by detecting a gaze-based command provided by the user. Such a gaze-based command may be detected by system 300 in any suitable manner. For example, system 300 may be configured to access, in any suitable manner, images generated by an imaging device provided within the stereoscopic image viewer of user control system 104. Based on the generated images, system 300 may determine a gaze point of the user's eye by determining a positional relationship between the pupil of the user's eye and a corneal reflection caused by infrared light provided by an infrared light source within user control system 104. System 300 may then infer the gaze point of the user's eye in any suitable manner based on the determined positional relationship.

When the gaze point of the user's eye dwells on the target object for a predetermined amount of time, system 300 may determine that the user of the computer-assisted surgical system intends to interact with the target object. The predetermined amount of time may correspond to any suitable amount of time that may be used to determine the intent of the user. For example, the predetermined amount of time may correspond to three seconds in certain implementations. In such an example, whenever the user's gaze point dwells on the target object for three or more seconds, system 300 may determine that the user intends to interact with the target object.

Additionally or alternatively, system 300 may be configured to detect the intent of the user based on a procedural context associated with a surgical space. To illustrate an example, a procedural context associated with a surgical space may be associated with use of a drop-in ultrasound probe within the surgical space. In such an example, system 300 may determine that a user intends to interact with the ultrasound probe based on a captured image of the surgical space that shows the ultrasound probe being present within the surgical space. In another example, a procedural context associated with a surgical space may be associated with a suturing operation to be performed in the surgical space. In such an example, system 300 may determine a user intends to interact with a non-robotic device such as suture needle based on the combination of a suture needle being detected in the surgical space and a needle driver robotic instrument being located in the surgical space and grasping the suture needle.

System 300 may detect the intent of the user to interact with a target object at any suitable time. For example, system 300 may detect the intent of the user after system 300 determines that the target object is located in the surgical space. Alternatively, system 300 may detect the intent of the user to interact with the target object before system 300 determines that the target object is located in the surgical space.

System 300 may further be configured to determine a pose of a target object within a surgical space. System 300 may determine the pose of a target object in any suitable manner. For example, the pose of a target object may be determined based on a combination of depth data (e.g., provided in a depth map of a surgical space) and a determined orientation of the target object within in the surgical space. Exemplary ways that system 300 may determine an orientation of a target object will now be described.

In certain examples, system 300 may determine an orientation of a target object by using a 3D model of the target object. System 300 may use a 3D mod& of a target object in any suitable manner to facilitate determining an orientation of the target object. For example, system 300 may be configured to access an image of a target object in a surgical space (e.g., an image captured by imaging device 202). System 300 may be configured to determine a representation (e.g., an outer contour shape) of the target object from a viewpoint of the imaging device. System 300 may use any suitable image processing algorithm to determine the representation of the target object. System 300 may compare the representation of the target object to a 2D projection of a 3D model of the target object that is oriented in a known orientation. System 300 may be configured to determine a projection error between the representation of the target object and the 2D projection of the 3D model. The projection error may correspond to any quantifiable metric that is indicative of a difference between an orientation of a representation of a target object and an orientation of a 2D projection of a 3D model. The greater the projection error, the less likely that the target object is oriented in the known orientation. As such, system 300 may determine that the target object is not in the known orientation when the projection error is above a predefined threshold.

System 300 may be configured to determine whether the projection error is less than a predefined threshold. If system 300 determines that the projection error is less than the predefined threshold, system 300 may then identify the target object as being oriented in the known orientation. On the other hand, if system determines that the projection error is not less than the predefined threshold, system 300 may change the orientation of the 3D model and generate an additional 2D projection of the 3D model of the target object that is oriented in an additional known orientation. System 300 may then determine an additional projection error between the representation of the target object and the additional 2D projection of the 3D model. System 300 may then repeat an operation to determine whether the additional projection error is less than the predefined threshold. System 300 may repeat such operations until the orientation of the target object is determined.

In addition to system 300 determining the orientation of the target object, system 300 may determine the position of the target object within the surgical space. This may be accomplished in any suitable manner. For example, system 300 may use depth data and/or any other suitable data to determine the position of the target object within the surgical space. System 300 may then determine the pose of the target object within the surgical space based on the combination of the determined orientation of the target object and the determined position of the target object within the surgical space.

In certain examples, system 300 may determine a pose of a target object based on the position of the target object within the surgical space and an orientation of one or more markers provided on an outer surface of a target object. In such examples, a particular orientation of one or more markers when viewed from a particular viewpoint may be indicative of a particular orientation of the target object within the surgical space. For example, two markers may be provided on an outer surface of a non-robotic device. A first orientation of the two markers may be indicative of a first orientation of the non-robotic device, a second orientation of the two markers may be indicative of a second orientation of the non-robotic device, and a third orientation of the two markers may be indicative of a third orientation of the non-robotic device. System 300 may detect whether the two markers are in the first orientation, the second orientation, or the third orientation in any suitable manner. For example, system 300 may analyze an image of the surgical space in any suitable manner to determine the orientation of the two markers from a particular viewpoint.

In certain examples, the one or more markers may also be used to identify the type of a non-robotic device located in a surgical space. For example, a particular type of a marker, position of a marker, combination of markers, and/or configuration of a marker may indicate the type of the non-robotic device. A marker provided on an outer surface of a target object may have any suitable configuration as may serve a particular implementation.

System 300 may detect the pose of a target object within a surgical space at any suitable time. In certain examples, system 300 may detect the pose of the target object within a surgical space after detecting the intent of a user to interact with the target object. Alternatively, system 300 may detect the pose after or concurrently with the detection of the target object being located in the surgical space.

In certain examples, the pose of a target object may change during a surgical procedure performed with respect to a surgical space. When the target object changes position and/or orientation within the surgical space, system 300 may determine an updated pose of the target object in the surgical space in any suitable manner, such as described herein. In certain examples, system 300 may be configured to continually monitor and update the pose of a target object during a surgical procedure. Alternatively, system 300 may periodically determine an updated pose of a target object.

In certain examples, system 300 may determine a pose that a robotic instrument is intended to assume to interact with a target object. System 300 may determine the pose that a robotic instrument is intended to assume in any suitable manner. For example, system 300 may access a database that includes a set of candidate orientations for the robotic instrument to assume to facilitate the robotic instrument interacting with the target object. Such a database may include any suitable number of candidate orientations as may serve a particular implementation. In certain examples, the database may include a plurality of candidate orientations for each possible orientation that a target object may have in a surgical space. For example, a first orientation of a target object in a surgical space may be associated with a first candidate orientation, a second candidate orientation, and a third candidate orientation of a robotic instrument. A second orientation of a target object in the surgical space may be associated with a fourth candidate orientation, a fifth candidate orientation, and a sixth candidate orientation of the robotic instrument. In such examples, system 300 may determine the orientation of the target object in any suitable manner. System 300 may then select the corresponding candidate orientations from the database that are associated with the determined orientation of the target object as being possible orientations for a robotic instrument to assume. Such a database may be maintained by storage facility 304 and/or may be maintained by any suitable storage device accessible by system 300.

System 300 may select an orientation from the set of candidate orientations included in the database. System 300 may select the orientation in any suitable manner. For example, system 300 may analyze a current pose (e.g., orientation and position) of a target object within the surgical space. Based on the current pose of the target object, system 300 may determine that the set of candidate orientations includes a first candidate orientation, a second candidate orientation, and a third candidate orientation that the robotic instrument may assume to facilitate interacting with the target object. System 300 may then select which of the first, second, or third candidate orientations of the robotic instrument included in the database is most conducive to the robotic instrument interacting with the target object. For example, system 300 may determine, in any suitable manner, that the first candidate orientation is easier for a user to achieve (e.g., based on the current orientation of the robotic instrument in the surgical space), results in a better interaction (e.g., a stronger grasp) with the target object, and/or results in better visibility in the surgical space than the second and third candidate orientations. Accordingly, system 300 may select the first candidate orientation as the orientation to be used for the robotic instrument to interact with the target object.

System 300 may select a position for the robotic instrument to assume within the surgical space in relation to the target object. System 300 may select the position for the robotic instrument to assume in any suitable manner. For example, system 300 may analyze depth data associated with the surgical space to determine a relative pose within the surgical space of the target object and/or other objects (e.g., anatomy, other robotic instruments, etc.). Based on the depth data, the selected orientation that the robotic instrument is intended to assume, and/or any other suitable information, system 300 may select a position for the robotic instrument to assume while the robotic instrument is in the selected orientation.

System 300 may determine the pose that the robotic instrument is intended to assume based on the selected orientation and the selected position.

In certain examples, system 300 may determine a pose that a robotic instrument is intended to assume based on a type of the target object located in the surgical space. To illustrate an example, a non-robotic device may correspond to a type of target object that is best grasped from a direction that is perpendicular to a lengthwise extension of the non-robotic device. Accordingly, system 300 may select an orientation for a robotic instrument to assume that is perpendicular to the lengthwise extension of the non-robotic device. In addition, the intended use of a non-robotic device may require maintaining visualization of the surface of an object (e.g., kidney 404) in a surgical space. Accordingly, system 300 may select the orientation of the robotic instrument so as to maximize viewability of the surface of the object during a surgical procedure (e.g., while robotic instrument 204-1 grasps and moves non-robotic device 402 within the surgical space). For example, the selected orientation and selected position may be provided on a side of a robotic instrument to maximize viewability of the surface of the object.

In certain examples, system 300 may be configured to generate a set of candidate orientations for a robotic instrument to assume to facilitate the robotic instrument interacting with a target object. For example, system 300 may be configured to generate a set of candidate orientations for the robotic instrument to assume to facilitate the robotic instrument interacting with the target object. System 300 may generate the set of candidate orientations in any suitable manner. For example, in certain implementations, system 300 may use machine learning to generate the set of candidate orientations and/or perform any other operation described herein.

In certain examples, system 300 may use a supervised machine learning algorithm to generate a database of candidate orientations for a robotic instrument. In such examples, the training inputs to the supervised machine learning algorithm may include a plurality of images of a surgical space that include labeled orientations of robotic instruments in relation to target objects. System 300 may use the supervised machine learning algorithm in any suitable manner during a training phase to analyze the plurality of images of one or more surgical spaces with the labeled orientations of robotic instruments. After the training phase, system 300 may obtain, as an operational input, an image of a surgical space in which a target object is located. System 300 may use the supervised machine learning algorithm in any suitable manner (e.g., by using a deep neural network) to analyze the image of the surgical space including the target object and generate a set of candidate orientations. System 300 may determine, from the set of candidate orientations, an optimal orientation (e.g., an optimal class of orientations) for a robotic instrument to assume to interact with a target object. In certain alternative implementations, system 300 may use an unsupervised machine learning algorithm to perform any of the operations described herein. System 300 may select an orientation from the generated candidate orientations, may select a position for the robotic instrument to assume within the surgical space in relation to the target object, may select the position, and may determine the pose that the robotic instrument is intended to assume based on the selected orientation and the selected position in any suitable manner, such as described herein.

After system 300 determines a pose for a robotic instrument to assume, system 300 may facilitate the robotic instrument assuming the pose. System 300 may facilitate the robotic instrument assuming the pose in any suitable manner. For example, in certain implementations, system 300 may facilitate the robotic instrument assuming the pose by generating a motion path for a robotic instrument to follow to assume a determined pose. System 300 may generate a motion path in any suitable manner. For example, system 300 may determine, in any suitable manner, a current pose of a robotic instrument. System 300 may generate a motion path that starts at the current pose of the robotic instrument and that extends in any suitable path within the surgical space to the determined pose to be assumed by the robotic instrument. In certain examples, system 300 may generate a plurality of motion paths for a robotic instrument to follow to assume the determined pose. System 300 may then select an optimal motion path included in the plurality of motion paths for the robotic instrument to follow.

System 300 may leverage any suitable information associated with a surgical space to facilitate selecting an optimal motion path for a robotic instrument to follow. For example, system 300 may take into consideration a configuration of a computer-assisted surgical system, kinematic constraints of one or more manipulator arms of the computer-assisted surgical system, environmental constraints of a surgical space, and/or any other suitable information.

In certain examples, system 300 may select an optimal motion path based on a collision factor associated with a surgical space. A collision factor may represent any aspect associated with a surgical space that may affect how feasible it is for a robotic instrument to travel unimpeded along a candidate motion path. For example, a collision factor may include information associated with a position of anatomy with respect the motion path, information associated with a position of another robotic instrument and/or another object with respect to the motion path, etc. System 300 may determine that a particular motion path would result in a robotic instrument undesirably contacting anatomy and/or another object (e.g., another robotic instrument). Accordingly, system 300 may determine such a motion path is undesirable based on such collision factors.

Additionally or alternatively, system 300 may select an optimal motion path based on an economy of motion factor of a robotic instrument. An economy of motion factor may represent any aspect that defines how much a robotic instrument is to move in the surgical space to assume a given pose. For example, an economy of motion factor may include a distance that a robotic instrument is to travel to interact with a target object and/or an amount an orientation of a robotic instrument is to change to assume a particular orientation. For example, a first candidate motion path may result in the robotic instrument traversing a first distance across the surgical space and a second candidate motion path may result in the robotic instrument traversing a second distance across the surgical space. The first distance may be greater than the second distance. As such, system 300 may determine that the second candidate motion path is preferable to the first candidate motion path.

Additionally or alternatively, system 300 may select an optimal motion path based on a field of view factor of the surgical space. A field of view factor may be indicative of how much of a given motion path is viewable within a field of view of the surgical space at a given time. In such examples, a first candidate motion path that is fully within a current field of view of the surgical space may be favored over a second candidate motion path that requires a change of the field of view to view all or part of the second candidate motion path.

In certain examples, system 300 may determine that there is an obstruction in a motion path. Such an obstruction may correspond to any object that may block a robotic instrument from following a motion path. For example, an obstruction may include anatomy, another robotic instrument, and/or any other object in the surgical space. System 300 may determine that there is an obstruction in any suitable manner. For example, system 300 may determine that there is an obstruction by analyzing a depth map of the surgical space, kinematics associated with one or more robotic instruments in the surgical space, and/or any other suitable information.

If system 300 determines that there is an obstruction in a motion path, system 300 may perform an operation to facilitate removal of the obstruction from the motion path. For example, system 300 may instruct a user (e.g., surgeon 110-1), in any suitable manner, to move a robotic instrument to a different location within the surgical space that does not obstruct the motion path. Alternatively, system 300 may instruct an additional user (e.g., assistant 110-2) to remove a robotic instrument from the surgical space.

In certain examples, system 300 may automatically perform an operation to remove an obstruction from a motion path. For example, system 300 may automatically reposition a robotic instrument within the surgical space such that the robotic instrument no longer obstructs a motion path.

In certain examples, system 300 may establish a no-fly zone within a surgical space. Such a no-fly zone may correspond to an area of the surgical space where a robotic instrument is not allowed to travel. System 300 may establish such a no-fly zone due to visibility restrictions, obstructions due to other robotic instruments, obstructions due to anatomy, and/or for any other suitable reason. In such examples, system 300 may take into consideration the no-fly zone when determining an optimal motion path for a robotic instrument to follow to assume a pose.

In implementations where system 300 generates a motion path for the robotic instrument to follow, system 300 may facilitate a robotic instrument automatically following the generated motion path to assume a pose. In such examples, system 300 may direct a computer-assisted surgical system (e.g., system 100) to automatically move the robotic instrument along the motion path without requiring input from the user.

In certain implementations, system 300 may facilitate the robotic instrument automatically following the motion path with various levels of autonomy. For example, in certain implementations, system 300 may direct a computer-assisted surgical system to which the robotic instrument is attached to automatically move robotic instrument along the motion path and assume the identified pose. Alternatively, system 300 may direct the computer-assisted surgical system to which the robotic instrument is attached to automatically move the robotic instrument along the motion path to a vicinity of the determined pose. Once the robotic instrument is in the vicinity of the determined pose, a user (e.g., surgeon 110-1) may then assume manual control and fine positioning of the robotic instrument (e.g., by using master controls of user control system 104) to adjust the position and orientation of the robotic instrument such that the robotic instrument assumes the determined pose.

In examples where system 300 automatically controls a robotic instrument, system 300 may automatically cause the robotic instrument to assume an orientation associated with a determined pose at any suitable time. For example, system 300 may cause the robotic instrument to first assume the orientation associated with the determined pose and then automatically follow the motion path to a position associated with the determined pose. Alternatively, system 300 may automatically cause the robotic instrument to follow the motion path and then assume the orientation associated with the determined pose upon the robotic instrument reaching the position associated with the determined pose. Alternatively, system 300 may cause the robotic instrument to assume the orientation associated with the determined pose while the robotic instrument is following the motion path.

In certain alternative implementations, system 300 may be configured to facilitate a user (e.g., surgeon 110-1) of a computer-assisted surgical system to which the robotic instrument is attached moving the robotic instrument along the motion path. System 300 may facilitate the user moving the robotic instrument along the motion path in any suitable manner. For example, in certain implementations, system 300 may be configured to provide virtual guidance to facilitate a user moving a robotic instrument along a motion path. In certain examples, such virtual guidance may include system 300 providing haptic feedback guidance in any suitable manner, such as described herein, to facilitate a user moving a robotic instrument along a motion path.

Additionally or alternatively, system 300 may be configured to provide audible guidance to facilitate a user moving a robotic instrument along a motion path. Such audible guidance may be provided in any suitable manner. For example, as the user moves a robotic instrument so as to follow a motion path, system 300 may provide audible guidance in the form of a "beep" noise or any other suitable noise whenever the user deviates from the motion path by more than some predefined threshold amount.

In certain examples, system 300 may generate one or more waypoints along a motion path to facilitate visualization of the motion path. System 300 may generate any suitable number of waypoints along a motion path as may serve a particular implementation. In certain examples, such waypoints may be provided for display to a user instead of or as part of a graphical depiction of a motion path. Such waypoints may have any suitable size and/or shape (e.g., circle, square, triangle, etc.) as may serve a particular implementation.

In certain examples, waypoints such as those described herein may be provided by system 300 as part of a supervised autonomous movement of the robotic instrument along the motion path. For example, system 300 may facilitate a user confirming that a motion path is acceptable at each waypoint provided along a motion path as a computer-assisted surgical system autonomously moves the robotic instrument along the motion path. In so doing, system 300 may receive real time confirmation from the user that a motion path is acceptable as a robotic instrument moves past each waypoint along the motion path. If there is a change in the surgical space that would affect the motion path (e.g., an obstruction is introduced after system 300 generates the motion path) as the robotic instrument moves along the motion path, system 300 may perform any suitable operation with respect to the change in the surgical space. In certain examples, system 300 may provide an augmented preview of a representation of the robotic instrument moving along the motion path to facilitate a user confirming that the motion path is acceptable.

In certain examples, system 300 may be configured to provide a notification to a user when a robotic instrument assumes a determined pose. Such a notification may be provided in any suitable manner. For example, system 300 may be configured to provide a visual notification, an audible notification, and/or a haptic feedback notification to a user when a robotic instrument assumes the determined pose. To illustrate an example, a user (e.g., surgeon 110-1) may control a robotic instrument so as to follow the motion path represented by a graphical depiction. At any suitable time during or after the movement of the robotic instrument to a position of the representation, the user may rotate the robotic instrument so that the robotic instrument assumes the orientation associated with the representation. When the position and orientation of the robotic instrument matches or is within some predefined threshold of the position and orientation of the representation, system 300 may provide, for example, an audio tone, a change the visual appearance (e.g., a change in color, pattern, etc.) of the representation, and/or haptic feedback in the form of vibration through the master controls of user controls system 104 to inform the user that the robotic instrument has assumed the pose and is ready to interact with (e.g., grasp) a non-robotic device.

In certain examples, a target object such as a non-robotic device may include a protrusion provided on an outer surface of thereof to facilitate a robotic instrument grasping the target object. In examples were a protrusion is provided on an outer surface of a non-robotic device, system 300 may take into consideration a pose of the protrusion when determining the pose that a robotic instrument will assume to interact with the non-robotic device. Any suitable number of protrusions may be provided on an outer surface of a non-robotic device as may serve a particular implementation. For example, in certain implementations, two or more protrusions may be provided an outer surface of a non-robotic device. In such examples, a robotic instrument may be configured to grasp any one of the multiple protrusions to facilitate moving the non-robotic device in the surgical space. In addition, a protrusion of a non-robotic device may have any suitable size and/or configuration to facilitate a robotic instrument attached to a computer-assisted surgical system grasping the non-robotic device.

In certain examples, system 300 may perform one or more operations to facilitate guided teleoperation of a device such as a non-robotic device in a surgical space. As used herein, "teleoperation of an device" such as a non-robotic device may refer to the indirect teleoperation of a non-robotic device by way of a robotic instrument attached to a computer-assisted surgical system. To that end, in certain examples, system 300 may generate guidance content associated with the non-robotic device. As used herein, "guidance content" may include any content that may be used by a computer-assisted surgical system to facilitate guided teleoperation of a non-robotic device in a surgical space. The generating of such guidance content by system 300 may include generating instructions and/or other guidance content for use by a computer-assisted surgical system, such as by generating computer-readable instructions for processing by the computer-assisted surgical system, and/or may include generating and/or accessing any suitable content to be presented by the computer-assisted surgical system (e.g., via a user interface associated with the computer-assisted surgical system).

Examples of guidance content may include, but are not limited to, virtual representations of robotic instruments, virtual representations of non-robotic devices, notifications, virtual pointers, animations, instructions, audible guidance, visual guidance, haptic feedback guidance, graphical depictions of suggested paths for a non-robotic device to follow, content configured to indicate a contact state of a non-robotic device with respect to an object in the surgical space, instructions usable by the computer-assisted surgical system to provide guidance content, and/or any combination thereof. Examples of guidance content that may be generated by system 300 to be presented by a computer-assisted surgical system may include, but are not limited to, suggested paths for a robotic instrument to follow within a surgical space, content configured to indicate a contact state of a non-robotic device with respect to an object in the surgical space, and/or any other generated content that may facilitate guided teleoperation of a non-robotic device. Specific examples of guidance content are described herein.

System 300 may generate guidance content at any suitable time. For example, system 300 may generate guidance content prior to a surgical procedure, during a surgical procedure, and/or at any other suitable time.

In certain examples, system 300 may generate at least some guidance content by accessing the guidance content from a storage device (e.g., storage facility 304) associated with a computer-assisted surgical system (e.g., surgical system 100). Examples of guidance content that may be accessed from a storage device may include, but are not limited to, graphical depictions of robotic instruments, non-robotic devices, and/or non-robotic devices that are engaged by (e.g., grasped by) robotic instruments, audible notifications, visual notifications, etc.

Guidance content may be generated based on any suitable parameters associated with a surgical space, such as described herein. For example, guidance content may be generated based on one or more of a procedural context associated with the surgical space, parameters of a non-robotic device (e.g., an identified type of non-robotic device, a pose of the non-robotic device, etc.), parameters of a robotic instrument (e.g., an identified type of robotic instrument, a pose of the robotic instrument, etc.), an indicated or a predicted use or operation of the non-robotic device, and/or any other suitable parameter or combination of parameters.

To illustrate an example, system 300 may access any suitable information associated with a surgical space to obtain a first parameter, a second parameter, and a third parameter associated with a non-robotic device located in the surgical space. Based on the first, second, and third parameters, system 300 may generate guidance content to facilitate teleoperation of the non-robotic device in the surgical space. For example, system may determine from the first, second, and third parameters that a visual notification in the form of a graphical overlay would be useful in facilitating teleoperation of the non-robotic device in the surgical space. Accordingly, system 300 may access the graphical overlay in any suitable manner for presentation by way of a computer-assisted surgical system. Based on the first, second, and third parameters, system 300 may also generate computer executable instructions that specify when the graphical overlay is to be provided for display, where the graphical overlay is to be provided for display, how long the graphical overlay is to be provided for display, etc. to facilitate teleoperation of the non-robotic device. Specific examples of how one or more parameters may be used to generate guidance content are described herein.

Guidance content generated by system 300 for presentation by a computer-assisted surgical system may be configured to be presented in any suitable manner. For example, in certain implementations, the guidance content may be configured to be presented by way of a user interface associated with a computer-assisted surgical system. To illustrate, system 300 may provide the guidance content for presentation by way of user control system 104 of surgical system 100 to facilitate a user, such as surgeon 110-1, teleoperating a non-robotic device. Additionally or alternatively, the guidance content may be provided for presentation by way of any other suitable user interface that may be associated with a computer-assisted surgical system. For example, guidance content may be provided to a user by way of a user interface associated with display monitor 114 of auxiliary system 106 in certain implementations.

In certain examples, system 300 may provide guidance content as visual guidance to facilitate a user (e.g., surgeon 110-1) of a computer-assisted surgical system teleoperating a non-robotic device in a surgical space. Such visual guidance may be provided in any suitable manner. For example, system 300 may instruct a computer-assisted surgical system to provide a blinking light and/or any suitable graphical object or augmented overlay for display to a user (e.g., to surgeon 110-1 by way of user control system 104) that guides the user in teleoperation of the non-robotic device in the surgical space.

Additionally or alternatively, system 300 may provide guidance content as audible guidance to facilitate a user of a computer-assisted surgical system teleoperating a non-robotic device in a surgical space. Such an audible guidance may be provided in any suitable manner. For example, an audible notification may include a "beep," playback of an audio clip with spoken language, and/or any other suitable audible guidance.

Additionally or alternatively, system 300 may be provide guidance content as haptic feedback guidance to facilitate a user of a computer-assisted surgical system teleoperating a non-robotic device. Such haptic feedback guidance may be provided in any suitable manner. For example, system 300 may instruct a computer-assisted surgical system to cause one of the master controls of user control system 104 to vibrate to inform the user regarding where or how to move a non-robotic device in a surgical space. Various examples of guidance content or combinations of guidance content that may be provided by system 300 are described herein.

In certain implementations, guidance content generated by system 300 may facilitate a non-robotic device making contact with an object, maintaining a predefined amount of contact with the object, and/or maintaining a predefined contact angle with respect to the surface of the object. Accordingly, in such examples, the guidance content may indicate at least one of a contact pressure or a contact angle of a non-robotic device with respect to a surface of an object and/or may indicate one or more operations to be performed to obtain and/or maintain a certain contact angle and/or contact pressure (e.g., within certain ranges of contact angles and/or contact pressures) between the non-robotic device and the object.

To illustrate an example, in certain implementations, a non-robotic device may correspond to a suture needle that is grasped by a robotic instrument in a surgical space. In such examples, system 300 may obtain and analyze any suitable parameter(s) associated with the suture needle and/or the surgical space (e.g., depth data, visible light imagery, force feedback data, etc.) to determine the contact state of the suture needle with respect to tissue (e.g., whether the suture needle is in contact with tissue to be sutured, the contact pressure of the suture needle, and/or the contact angle of the suture needle with respect to the tissue). System 300 may then generate guidance content in any suitable manner to facilitate a user performing a suturing procedure with the suture needle. For example, system 300 may generate visual guidance in the form of a graphical overlay to be provided for display by way of the stereoscopic image viewer of user control system 104. Such visual guidance may instruct the user to move a robotic instrument in a specific manner to adjust the contact pressure of the suture needle with respect to the tissue to be sutured, move the robotic instrument to adjust the contact angle of the suture needle with respect to the tissue to be sutured, change a suturing position of the suture needle, and/or perform any other suitable action.

In certain examples, guidance content generated by system 300 may include a suggested path (may also referred to herein as a motion path) for a non-robotic device to follow in a surgical space while the non-robotic device is engaged by a robotic instrument in the surgical space. In certain examples, system 300 may be configured to generate a plurality of suggested paths for a non-robotic device to follow in a surgical space. For example, a first suggested path may start at a current position of a non-robotic device in a surgical space and may end at a first position on a surface of an object in the surgical space. A second suggested path may start at the first position on the surface of the object and extend to a second position on the surface of the object.

System 300 may generate guidance content in the form of a suggested path in any suitable manner, such as described herein.

In certain alternative examples, system 300 may generate a suggested path for a non-robotic device to follow based on input provided by a user. To that end, system 300 may be configured to facilitate a user defining at least some portions of a suggested path prior to system 300 generating the suggested path. System 300 may facilitate a user providing input to define at least a part of a suggested path in any suitable manner. For example, system 300 may facilitate a user defining a first virtual pointer indicative of a start position of a suggested path and a second virtual pointer indicative of a stop point of the suggested path. System 300 may facilitate a user selecting a position of virtual pointers in a surgical space in any suitable manner. For example, a user (e.g., surgeon 110-1) may be able to move a cursor by manipulating master controls of user control system 104 to position the virtual pointers with respect to an object in a surgical space. Alternatively, a user (e.g., assistant 110-2) may define virtual pointers through any suitable input (e.g., mouse cursor input, touch input, etc.) entered by way of any suitable display (e.g., display monitor 114) associated with a computer-assisted surgical system.

Additionally or alternatively, guidance content may include a graphical depiction of a suggested path provided for display by way of a display device associated with a computer-assisted surgical system. In addition to providing such a graphical depiction as part of guidance content, system 300 may provide additional guidance content associated with a suggested path, such as by concurrently providing additional guidance content to facilitate a non-robotic device moving along a suggested path. For example, in certain implementations such additional guidance content may include providing a notification to the user of a computer-assisted surgical system that requests user confirmation that the suggested path indicated by, for example, a graphical depiction is acceptable. Such a notification may be provided to a user in any suitable manner. For example, system 300 may access an audible notification from a storage device associated with a computer-assisted surgical system. System 300 may instruct the computer-assisted surgical system to display a graphical depiction of the suggested path and playback an audio clip with the expression "please confirm that the suggested path is acceptable." The user may then visually examine the suggested path represented by a graphical depiction to determine whether the suggested path is free of obstructions and/or is otherwise acceptable. If the user determines that the suggested path is acceptable, the user may provide any suitable response to the audio clip. For example, the user may say "yes" out loud to indicate that the suggested path represented by the graphical depiction is acceptable. In such an example, system 300 may use any suitable speech recognition algorithm to detect the response of the user. Additionally or alternatively, system 300 may access any suitable text notification that a computer-assisted surgical system may provide for display to a user to request user confirmation that a suggested path is acceptable.

Additionally or alternatively, guidance content provided by system 300 may include content that facilitates a user moving a non-robotic device along a suggested path. For example, in certain implementations, system 300 may be configured to provide virtual guidance to facilitate a user moving a non-robotic instrument along a suggested path. In certain examples, such virtual guidance may include system 300 providing haptic feedback guidance. Such haptic feedback guidance may be provided in any suitable manner. For example, such haptic feedback guidance may correspond to a virtual fixture such as a haptic feedback tunnel in the surgical space that is configured to guide control of the non-robotic instrument and/or the robotic instrument engaging the non-robotic instrument along a suggested path in the surgical space. With such a haptic feedback tunnel, as the user moves a non-robotic instrument along a suggested path, system 300 may provide haptic feedback in the form of vibration of the master controls of user control system 104 whenever the non-robotic instrument and/or the robotic instrument engaging the non-robotic instrument deviates from the suggested path by more than some predefined threshold amount.

In certain examples, it may be helpful for a user to visualize a non-robotic device moving along a suggested path prior to the non-robotic device moving along the suggested path. Accordingly, in certain examples, guidance content generated by system 300 in relation to a suggested path may additionally or alternatively include a simulation of the non-robotic device moving along the suggested path. In certain examples, such a simulation may include a virtual representation of a non-robotic device. As used herein, a "virtual representation of a non-robotic device" may correspond to any suitable indicator that may be used to represent a non-robotic device and/or inform a user of a position, orientation, or pose that a non-robotic device is intended to assume with respect to an object at any point along the suggested path. In certain examples, a virtual representation of a non-robotic device may also include a virtual representation of a robotic device that is engaged with (e.g., that is grasping) the non-robotic device. A virtual representation of a non-robotic device may have any suitable shape, size, and/or visual appearance as may serve a particular implementation. For example, a virtual representation of a non-robotic device may be transparent, translucent, opaque, colored, and/or patterned. In certain examples, a virtual representation of a non-robotic device may have a 3D appearance when displayed by a display device associated with a computer-assisted surgical system. Such a virtual representation of a non-robotic device may be provided for display in any suitable manner. For example, a computer-assisted surgical system may provide the virtual representation as a graphical overlay over an endoscopic view of the surgical space displayed to surgeon 110-1 by way of user control system 104.

After system 300 generates guidance content such as described herein, system 300 may provide the guidance content to a computer-assisted surgical system (e.g., surgical system 100). This may be accomplished in any suitable manner. For example, system 300 may transmit the guidance content in any suitable manner (e.g., by way of a wired and/or a wireless connection) by way of any suitable communication interface associated with a computer-assisted surgical system. The computer-assisted surgical system may use the guidance content in any suitable manner, such as described herein, to facilitate guided teleoperation of a non-robotic device (e.g., while the non-robotic device is grasped by a robotic instrument) in a surgical space.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 11:
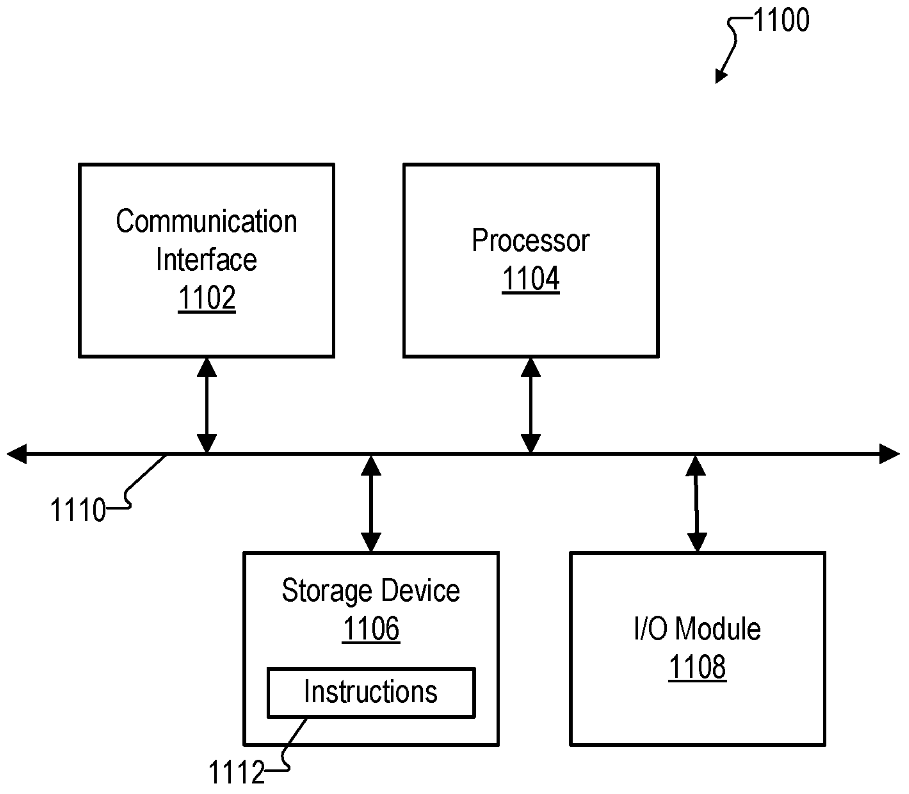
FIG. 11 illustrates an exemplary computing device according to principles described herein.

FIG. 11 illustrates an exemplary computing device 1100 that may be specifically configured to perform one or more of the processes described herein. As shown in FIG. 11, computing device 1100 may include a communication interface 1102, a processor 1104, a storage device 1106, and an input/output ("I/O") module 1108 communicatively connected one to another via a communication infrastructure 1110. While an exemplary computing device 1100 is shown in FIG. 11, the components illustrated in FIG. 11 are not intended to be limiting. Additional or alternative components may be used in other embodiments. Components of computing device 1100 shown in FIG. 11 will now be described in additional detail.

Communication interface 1102 may be configured to communicate with one or more computing devices. Examples of communication interface 1102 include, without limitation, a wired network interface (such as a network interface card), a wireless network interface (such as a wireless network interface card), a modem, an audio/video connection, and any other suitable interface.

Processor 1104 generally represents any type or form of processing unit capable of processing data and/or interpreting, executing, and/or directing execution of one or more of the instructions, processes, and/or operations described herein. Processor 1104 may perform operations by executing computer-executable instructions 1112 (e.g., an application, software, code, and/or other executable data instance) stored in storage device 1106.

Storage device 1106 may include one or more data storage media, devices, or configurations and may employ any type, form, and combination of data storage media and/or device. For example, storage device 1106 may include, but is not limited to, any combination of the non-volatile media and/or volatile media described herein. Electronic data, including data described herein, may be temporarily and/or permanently stored in storage device 1106. For example, data representative of computer-executable instructions 1112 configured to direct processor 1104 to perform any of the operations described herein may be stored within storage device 1106. In some examples, data may be arranged in one or more databases residing within storage device 1106.

I/O module 1108 may include one or more I/O modules configured to receive user input and provide user output. One or more I/O modules may be used to receive input for a single virtual experience. I/O module 1108 may include any hardware, firmware, software, or combination thereof supportive of input and output capabilities. For example, I/O module 1108 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1108 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1108 is configured to provide graphical data to a display for presentation to a user. The graphical data may be representative of one or more graphical user interfaces and/or any other graphical content as may serve a particular implementation.

In some examples, any of the systems, computing devices, and/or other components described herein may be implemented by computing device 1100. For example, storage facility 304 may be implemented by storage device 1106, and processing facility 302 may be implemented by processor 1104.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:

a memory storing instructions; and a processor communicatively coupled to the memory and configured to execute the instructions to:

obtain one or more operating characteristics of a device located in a surgical space, wherein the device is engaged with a first robotic instrument attached to a computer-assisted surgical system and master controls of the computer-assisted surgical system are configured for bimanual control of no more than two robotic instruments at a time;

obtain one or more anatomical characteristics associated with the surgical space, the one or more anatomical characteristics including depth map data of the surgical space; and direct the computer-assisted surgical system to automatically perform, without requiring further input from a user of the computer-assisted surgical system and based on the one or more operating characteristics of the device and the one or more anatomical characteristics associated with the surgical space, an operation with the device located in the surgical space, wherein:

the master controls of the computer-assisted surgical system are currently configured for bimanual control of a second robotic instrument and a third robotic instrument attached to the computer-assisted surgical system;

operation of the first robotic instrument is configured only for automatic control by the computer-assisted surgical system while the master controls are configured for bimanual control of the second robotic instrument and the third robotic instrument; and the directing of the computer-assisted surgical system to automatically perform the operation includes directing the computer-assisted surgical system to automatically control operation of the first robotic instrument in the surgical space based on the one or more operating characteristics and the one or more anatomical characteristics while the second robotic instrument and the third robotic instrument are bimanually teleoperated by the user of the computer-assisted surgical system.

2. The system of claim 1, wherein:

the obtaining of the one or more anatomical characteristics includes deriving the one or more anatomical characteristics based on one or more data streams associated with the surgical space; and the one or more data streams are configured to provide at least one of imaging data, kinematics data, procedural context data, or user input data associated with the surgical space.

3. The system of claim 2, wherein the one or more anatomical characteristics further include at least one of surface contour data or three-dimensional (3D) tissue position data associated with the surgical space.

4. The system of claim 1, wherein:

the processor is further configured to execute the instructions to apply, based on the one or more operating characteristics of the device and the one or more anatomical characteristics associated with the surgical space, an operating constraint to the device located in the surgical space;

the operating constraint is associated with constraining movement of the device in the surgical space; and the directing of the computer-assisted surgical system to automatically perform the operation includes directing the computer-assisted surgical system to change a pose of the device from a first pose to a second pose and maintain the device in the second pose during at least part of a surgical procedure performed in the surgical space.

5. The system of claim 1, wherein:

the processor is further configured to execute the instructions to apply, based on the one or more operating characteristics of the device and the one or more anatomical characteristics associated with the surgical space, an operating constraint to the device located in the surgical space;

the operating constraint is associated with constraining movement of the device in the surgical space; and the directing of the computer-assisted surgical system to automatically perform the operation includes directing the computer-assisted surgical system to automatically move the device in the surgical space based on movement of a robotic instrument to which the device is not attached.

6. The system of claim 1, wherein:

the processor is further configured to execute the instructions to apply, based on the one or more operating characteristics of the device and the one or more anatomical characteristics associated with the surgical space, an operating constraint to the device located in the surgical space;

the operating constraint is associated with constraining movement of the device in the surgical space; and the directing of the computer-assisted surgical system to automatically perform the operation includes directing the computer-assisted surgical system to automatically maintain the device at a rigid offset with respect to a robotic instrument to which the device is not attached.

7. The system of claim 1, wherein:

the processor is further configured to execute the instructions to apply, based on the one or more operating characteristics of the device and the one or more anatomical characteristics associated with the surgical space, an operating constraint to the device located in the surgical space;

the operating constraint is associated with constraining movement of the device in the surgical space; and the directing of the computer-assisted surgical system to automatically perform the operation includes directing the computer-assisted surgical system to maintain at least one of a contact pressure or a contact angle of the device with respect to a surface of an object in the surgical space.

8. The system of claim 1, wherein:

the device is a non-robotic device that is engaged by a robotic instrument attached to the computer-assisted surgical system; and the directing of the computer-assisted surgical system to automatically perform the operation includes directing the computer-assisted surgical system to automatically control, by way of the robotic instrument, operation of the non-robotic device in the surgical space.

9. The system of claim 1, wherein:

the device is a non-robotic imaging device that is engaged by a robotic instrument attached to the computer-assisted surgical system, the non-robotic imaging device configured to capture imagery of an object in the surgical space; and the directing of the computer-assisted surgical system to automatically perform the operation includes directing the computer-assisted surgical system to automatically control the non-robotic imaging device to capture the imagery of the object.

10. The system of claim 9, wherein:

the non-robotic imaging device is configured to contact a surface of the object to capture the imagery of the object; and the directing of the computer-assisted surgical system to automatically perform the operation includes directing the computer-assisted surgical system to maintain a state of contact of the non-robotic imaging device with the surface of the object.

11. The system of claim 10, wherein the maintaining of the state of contact includes:

determining, based on the one or more anatomical characteristics, that there will be a change in at least one of a contact pressure or a contact angle of the non-robotic imaging device with respect to the object as the non-robotic imaging device moves along the surface of the object; and automatically moving, in response to the determining that there will be the change, the non-robotic imaging device to maintain at least one of an amount of contact pressure or the contact angle of the non-robotic imaging device with respect to the object while the non-robotic imaging device moves along the surface of the object to capture the imagery of the object.

12. The system of claim 11, wherein the automatically moving of the non-robotic imaging device includes:

analyzing an image captured by the non-robotic imaging device while the non-robotic imaging device is used to capture the imagery of the object;

determining, based on the analyzing of the image captured by the non-robotic imaging device, that the image includes an image capture deficiency; and automatically adjusting the at least one of the contact pressure or the contact angle based on the image capture deficiency to maintain the at least one of the amount of contact pressure or the contact angle.

13. The system of claim 1, wherein the directing of the computer-assisted surgical system to automatically perform the operation includes directing the computer-assisted surgical system to:

generate a motion path for the device to follow in the surgical space; and automatically move the device along the motion path during a surgical procedure.

14. A system comprising:

a memory storing instructions; and a processor communicatively coupled to the memory and configured to execute the instructions to:

obtain one or more operating characteristics of a first robotic instrument in a surgical space, wherein the first robotic instrument, a second robotic instrument, and a third robotic instrument are each attached to a computer-assisted surgical system, wherein master controls of the computer-assisted surgical system are configured for bimanual control of no more than two robotic instruments at a time, the master controls of the computer-assisted surgical system are currently configured for bimanual control of a second robotic instrument and a third robotic instrument attached to the computer-assisted surgical system; and operation of the first robotic instrument is configured only for automatic control by the computer-assisted surgical system while the master controls are configured for bimanual control of the second robotic instrument and the third robotic instrument;

obtain one or more anatomical characteristics associated with the surgical space, the one or more anatomical characteristics including depth map data of the surgical space; and direct the computer-assisted surgical system to automatically perform, without requiring further input from a user of the computer-assisted surgical system and based on the one or more operating characteristics of the first robotic instrument and the one or more anatomical characteristics associated with the surgical space, an operation with the first robotic instrument based on the one or more operating characteristics and the one or more anatomical characteristics while the user of the computer-assisted surgical system bimanually teleoperates the second and third robotic instruments.

15. A method comprising:

obtaining, by a processor associated with a computer-assisted surgical system, one or more operating characteristics of a device located in a surgical space, wherein the device is engaged with a first robotic instrument attached to a computer-assisted surgical system and master controls of the computer-assisted surgical system are configured for bimanual control of no more than two robotic instruments at a time;

obtaining, by the processor, one or more anatomical characteristics associated with the surgical space, the one or more anatomical characteristics including depth map data of the surgical space; and directing, by the processor, the computer-assisted surgical system to automatically perform, without requiring further input from a user of the computer-assisted surgical system and based on the based on the one or more operating characteristics of the device and the one or more anatomical characteristics associated with the surgical space, an operation with the device located in the surgical space, wherein:

the master controls of the computer-assisted surgical system are currently configured for bimanual control of a second robotic instrument and a third robotic instrument attached to the computer-assisted surgical system;

operation of the first robotic instrument is configured only for automatic control by the computer-assisted surgical system while the master controls are configured for bimanual control of the second robotic instrument and the third robotic instrument; and the directing of the computer-assisted surgical system to automatically perform the operation includes directing the computer-assisted surgical system to automatically control operation of the first robotic instrument in the surgical space based on the one or more operating characteristics and the one or more anatomical characteristics while the second robotic instrument and the third robotic instrument are bimanually teleoperated by the user of the computer-assisted surgical system.

16. The method of claim 15, wherein:

the device is a non-robotic imaging device configured to contact a surface of an object in the surgical space to capture imagery of the object; and the directing of the computer-assisted surgical system to automatically perform the operation includes directing the computer-assisted surgical system to maintain a state of contact of the non-robotic imaging device with the surface of the object.

17. The method of claim 16, wherein the maintaining a state of contact includes the computer-assisted surgical system automatically adjusting at least one of contact pressure or a contact angle of the non-robotic imaging device with respect to the object while the non-robotic imaging device captures the imagery of the object.

18. The method of claim 17, wherein the automatically adjusting of the at least one of the contact pressure or the contact angle includes:

analyzing an image captured by the non-robotic imaging device while the non-robotic imaging device is used to capture the imagery of the object;

determining, based on the analyzing of the image captured by the non-robotic imaging device, that the image includes an image capture deficiency; and automatically adjusting the at least one of the contact pressure or the contact angle based on the image capture deficiency.

* * * * *